United States Patent
Valdes Sosa et al.

(10) Patent No.: US 7,092,748 B2
(45) Date of Patent: Aug. 15, 2006

(54) SYSTEM AND METHOD FOR THE TOMOGRAPHY OF THE PRIMARY ELECTRIC CURRENT OF THE BRAIN AND OF THE HEART

(75) Inventors: Petro Antonio Valdes Sosa, C. Habana (CU); Jorge Francisco Bosch Bayard, C. Habana (CU); Eduardo Francisco Aubert Vazquez, C. Habana (CU); Trinidad Virues Alba, C. Habana (CU); Frank Morales Aguilera, C. Habana (CU); Nelson Jesus Trujillo Barretto, Sancti Spirtus (CU); Jorge Miguel Soler McCook, C. Habana (CU); Jorge Javier Riera Diaz, La Habana (CU); Maria Elena Fuentes Montero, C. Habana (CU)

(73) Assignee: Centro Nacional de Investigaciones Cientificas (CNIC) (CU)

( * ) Notice: Subject to any disclaimer, the term of this patent is extended or adjusted under 35 U.S.C. 154(b) by 0 days.

(21) Appl. No.: 10/206,006

(22) Filed: Jul. 26, 2002

(65) Prior Publication Data

US 2003/0093004 A1 May 15, 2003

Related U.S. Application Data

(63) Continuation-in-part of application No. 09/507,312, filed on Feb. 18, 2000, now abandoned.

(51) Int. Cl.
*A61B 5/00* (2006.01)
(52) U.S. Cl. .................................... 600/407
(58) Field of Classification Search ............... 600/544, 600/545, 409, 426, 407
See application file for complete search history.

(56) References Cited

U.S. PATENT DOCUMENTS

| | | | | |
|---|---|---|---|---|
| 4,201,224 A | * | 5/1980 | John | 600/544 |
| 4,408,616 A | * | 10/1983 | Duffy et al. | 600/544 |
| 4,416,288 A | * | 11/1983 | Freeman | 600/544 |
| 4,417,592 A | * | 11/1983 | John | 600/544 |
| 4,545,388 A | | 10/1985 | John | |
| 4,736,751 A | * | 4/1988 | Gevins et al. | 600/545 |
| 4,753,246 A | * | 6/1988 | Freeman | 600/544 |
| 4,815,474 A | | 3/1989 | Duffy | |
| 4,841,983 A | | 6/1989 | Duffy | |
| 4,844,086 A | | 7/1989 | Duffy | |

(Continued)

*Primary Examiner*—Ali Imam
(74) *Attorney, Agent, or Firm*—Lackenbach Siegel LLP

(57) ABSTRACT

A three-dimensional map of the probability of brain or heart functional states is obtained based on electric or magnetic signals, or a combination of both measured in the surface of body. From signals, the statistical descriptive parameters are obtained and a map of its distribution is calculated. The map is the inverse solution of the problem based upon: a) the restriction of the solution to structures with high probability of generating electric activity using for this restriction an Anatomical Atlas and b) imposing that the solution belong to a pre-specified functional space. The probability is determined that this map belongs to a test group. The spatial and temporal correlations of the map are modeled as well as their dependence on experimental covariables. The resulting probabilities are coded in a pseudocolor scale and they are superimposed on a Anatomical Atlas for their interactive three-dimensional visualization.

20 Claims, 12 Drawing Sheets

U.S. PATENT DOCUMENTS

| | | | |
|---|---|---|---|
| 4,913,160 A * | 4/1990 | John | 600/544 |
| 4,949,725 A * | 8/1990 | Raviv et al. | 600/544 |
| 4,977,896 A * | 12/1990 | Robinson et al. | 600/409 |
| 4,991,579 A * | 2/1991 | Allen | 600/426 |
| 4,995,395 A * | 2/1991 | Ilmoniemi et al. | 600/409 |
| 5,083,571 A | 1/1992 | Prichep | |
| 5,282,474 A | 2/1994 | Valdes Sosa et al. | |
| 5,307,807 A * | 5/1994 | Valdes Sosa et al. | 600/409 |
| 5,797,853 A * | 8/1998 | Musha et al. | 600/544 |
| 2003/0004652 A1 * | 1/2003 | Brunner et al. | 702/19 |
| 2003/0050527 A1 * | 3/2003 | Fox et al. | 600/13 |

* cited by examiner a)

b)

c)

d)

SYSTEM AND METHOD FOR THE TOMOGRAPHY OF THE PRIMARY ELECTRIC CURRENT OF THE BRAIN AND OF THE HEART

This application is a Continuation-in-Part of U.S. patent application Ser. No. 09/507,312 filed on Feb. 18, 2000, now abandoned which claims priority from PCT/CU98/00006 filed Aug. 24, 1998, which in turn claims priority from Cuba Patent Application Ser. No. 87/97 filed Aug. 22, 1997, the contents of each are incorporated herein by reference.

BACKGROUND OF THE INVENTION

1. Field of the Art

The present invention consists of a system and method for obtaining Tomographic Images of the Primary Electric Currents (PEC) produced by the neurons of the brain and the muscle cells of the heart.

2. Description of the Prior Art

In this invention reference will be made to phrases and terms used of art that will be defined as follows:

Vectors will usually be denoted with boldface lowercase letters and matrices usually with uppercase boldface letters. $1_N$ is the vector of dimension N of ones. $I_n$ denotes the identity matrix of order n. $\otimes$ is the matrix Kronecker product. ".*" is the Hadamaard product and o represents the dyadic product among vectors. If x is a matrix or a vector, then $x^t$ denotes x transposed x; $x^*$ denotes x conjugate transposed. The operation vech(X) applied to X consists of forming a vector with the columns of X, eliminating repeated elements or those considered constant in the context of the problem.

Primary Electric Current (PEC) $j_P(r,t)$: is the macroscopic magnitude obtained by the spatial and temporal average of the post-synaptic activity of a group of nervous or heart cells at the position $\vec{r}$ and the instant of time t.

Volume Conductor $\Omega_V$: the region inside the body that will be the object of study (e.g., the head and/or the torso).

Generating Volume $\Omega_g$: the subset of $\Omega_V$ where the PEC originates (i.e., the brain or the heart).

Lattice of the Volume Conductor $\Re_V$: the discrete group of $N_V$ points $r_v \in \Omega_V$.

Lattice of the Generating Volume $\Re_g$: the discrete group of $N_g$ points $r_g \in \Omega_g$.

Lattices of Time Instants $\Im_m(t_I, I=1, \ldots, N_I^m)$: time scale for which each selected functional image m has been sampled.

Analysis Interval $\Im=[0,T]$ is the period defined from a reference fixed arbitrarily at the instant 0 until time T.

PEC Tomographic Image (TPEC): vector $j(t)=\lfloor j_P(\vec{r}_g,t)\rfloor_{1\leq g\leq N_g}$ defined at the points $r_g \in \Omega_g$, and for each instant $t\in \Im$ of time.

Electro-encephalogram (EEG) and Electro-cardiogram (EKG): time series obtained by measuring, on the head and the thorax respectively, the voltage difference $V_{er}(t)$ that is created in a pair of electrodes localized on the body in the positions $r_e$ (recording electrode) and $r_r$ (reference). $V_{er}(t)$ is measured at $N_e$ sites on the body. A vector of measurements of this type will be denoted by v(t).

Magneto-encephalogram (MEG) and Magneto-cardiogram (MKG): time series obtained by measuring the projection $b_{cn}(t)$ of the magnetic field density vector at the center $r_c$ of a simple coil on $n_c$, the perpendicular vector to the plane that contains it. These simple coils are connected to Superconducting Quantum Interference Devices (dc SQUID) by means of a group of magnetic flow detection transformers. $b_{cn}(t)$ are measured at $N_c$ sites of the body. The vector of measurements of this type will be denoted by b(t).

Anatomical Images: type of medical images that offer structural information about the body such as Computed Axial Tomography (CAT), Magnetic Resonance Images (MRI), post-mortem sections of the head using cryotomy, etc.

Anatomical Atlas: is an anatomical image of the brain or of the heart in a reference system of the head or the torso, respectively. A particular instance of a reference system for the brain is the "Talairach" international system. Possible types of anatomical atlases are:

Individual: structural images of the subject under study (FIG. 1); and

Probabilistic: a composite statistical image that summarizes the inter-individual variability of normal or pathological morphologies of anatomical images in a given population (Valdés P. and Biscay R. The statistical analysis of brain images. In: Machinery of the Mind, E. Roy John et al. the. (ed.), (1990). Birkhauser, pp. 405–434.; Collins D L, Neelin P, Peter T M, Evans A C (1994) Automatic 3D registration of MR volumetric dates in standardized talairach space. J Comput. Assist. Tomogr. 18(2): 192–205; Evans A C, Collins D L, Mills S R, Brown E D, Kelly R L, Peters T M (1993) 3D statistical neuroanatomical models from 305 MRI volumes. Proc. IEEE-nuclear Science Symposium and Medical Imaging Conference: 1813–1817; Evans, A. C., Collins, D. L., Neelin, P., MacDonald, D., Kambei, M., and Marret, T. S. (1994) Three dimensional correlative imaging: Applications in human brain mapping. In R. Thatcher, M. Hallet, T. Zeffiro, E. Roy John and M. Huerta (Eds.) Functional neuroimaging technological foundations. (Academic Press).

Functional Images: types of medical images that offer information on the hemodynamics corporal metabolism such as: Functional Magnetic Resonance (fMRI), Positron Emission Tomography (PET), and the Single Photon Emission Tomography (SPECT).

Observations $o(t)=[o(t)_m]_{1 \leq m \leq M}$ the group of M measurements of different modalities (EEG, MEG, and functional image) that will be used for the construction of the TPEC. All the measurements are referred to the reference system of the selected anatomical atlas. The EEG/EKG ($o_1(t)$) and/or the MEG/MKG ($o_2(t)$) and optionally the fMRI, PET, and SPECT ($o_m(t)$, m>2) will be always included in o(t). These observations are defined for the lattices of sensor positions $\aleph_m$ as the set of Cartesian coordinates that define the position and orientation of each sensor in a predefined common body reference system, said lattices being designated $\aleph_1$, $\aleph_2$, $\aleph_3$, $\aleph_4$, and $\aleph_5$ for the EEG/EKG, MEG/MKG, fMRI, PET, and SPECT, respectively. Alternatively, o(t) may be defined for the coordinates $y \in \Delta_m$, where $\Delta_m$ is the Space of Measurement of the modality m.

Multivariate Z Transform of the vector of random variables $x\Theta_x=\{\mu_x, \Sigma_x\}$, their mean vector and matrix of population covariances is defined $$z^X = (x - \mu_x) \cdot \sum_x^{-\frac{1}{2}}.$$

In this last expression one of the square roots of $\Sigma_x$ is selected and, if this is not of complete range, a pseudoinverse is used. In the case that x is of dimension 1, its Z Transform has the simple expression $$z^X = \frac{x - \mu_x}{\sigma_x}.$$

Generalized Gaussian Distribution $N_t^{k,p}(\mu_x, \Sigma_x)$: is a probability density proportional to $\exp(-\beta\|x-\mu_x\|_{\Sigma_x}^p)$, where k is the dimension of the distribution, p the order of the norm in the exponent $\|x-\mu_x\|_{\Sigma_x}^p = |z_x|^p$, $\beta$ a proportionality constant, and t is the numeric variable type (i.e., R—real or C—complex). For example, the notation $x \sim N_R^{2,p}(\mu_x, \Sigma_x)$ is used to express that x is a sample from a multivariate real gaussian distribution.

Functional Space: is a set of functions with common properties (Triebel, H. 1990. Theory of Function Spaces II. Basel: Birkhauser). Membership in a function space is used to specify desirable properties in the TPEC under consideration. The function spaces are considered to be consisting of the combination of atoms.

Dictionary of Atoms: is a collection of atoms with properties such that all element of a function space can be expressed as $$f = \sum_k F_k \cdot \psi_k,$$

where $\psi_k$ are the atoms. Examples are: "Wavelets", (Meyer, Y. 1992. Wavelets and Operators. Cambridge: Cambridge University Press), the Fourier base of complex exponential, the collection of Dirac deltas in a space of generalized functions, etc. A Megadictionary is the union of several dictionaries of atoms.

Besov Space $B_{n,s}^m(\Omega \to R^n)$: is a collection of functions defined on the space $\Omega$ and taking values in $R^n$ that possess a degree of smoothness specified by means of the triple (m, n, s) (Triebel, H. 1990. Theory of Function Spaces II. Basel: Birkhauser). The requirement that any given function f belongs to $B_{n,s}^m$ shall be imposed by means of penalization with the metric $$\|f\|_{B_{n,s}^m} \approx \|f\|_{b_{n,s}^m} = \sum_k a_k \cdot \|F_k\|^m,$$

that is to say the norm of weighted combination of the atoms (De Vore R. A. and Popov V., (1988) Interpolation of Besov Spaces, Transactions of the American Mathematical Society 305, 397–414). These spaces allow the modeling of functions with controllable degree of spatial inhomogeneity. Particular cases are:

Sobolev Space: $B_{2,2}^m = H^m$, of maximum smoothness (with respect to derivatives of order m); and The "algebra of bumps": $B_{1,s}^1$ that allows modeling both of point sources (dipoles) and distributed sources in a common framework. (Meyer Y., (1992) Wavelets and Operators, Cambridge: Cambridge University Press).

Reference group: consists of a reference group, the membership to which is to be established for a given TPEC image.

Classical Quantitative Electrophysiology (qEEG/qEKG)

This invention has as antecedents the work directed to quantify and to make objective the detection of abnormal states of the brain and heart by applying multivariate statistical analysis to the EEG and EKG. These methods are known as quantitative electroencephalography and quantitative electrocardiography (abbreviated respectively as qEEG and qEKG). Systems and methods for qEEG were described in the patents U.S. Pat. No. 4,846,190; U.S. Pat. No. 4,913,160; U.S. Pat. No. 5,282,474 and U.S. Pat. No. 5,083,571. Methods for qEKG were described in the U.S. Pat. No. 4,974,598. These patents specify recording of the EEG and/or EKG (v(t)) by means of a plurality of sensors.

Optionally, instead of analyzing the v(t) recorded originally, pre-processed series (PPS) are obtained by means of the calculation of the cross-covariance function of v(t) with respect to a time series s(t), marker of external events. In the case of the EEG, s(t) may be taken as a sequence of Dirac delta functions indicative of the moments at which certain stimuli are presented to the subject examined. The resulting time series is known as the Average Evoked Potential (AEP). In the case of the EKG, s(t) may signal the occurrence of the R wave of the EKG itself and the resulting PPS is the average EKG (AEKG).

The extraction of Descriptive Parameters (DP) from these time series are statistical summarizations of the recorded time series designed to reflect variations in normal and pathological physiological activity.

In the above-mentioned patents, the DP specified for the EEG are the averages in broad bands of the frequency of spectrum, and elementary transformations of these DP are also included. The DP of the Broad Band Spectral Analysis (BBSA) are defined formally as follows: $S_O(\omega)$ is the crosspectral or variance and covariances matrices of the coefficients of Fourier of V(t) (where $\omega$ denotes frequency). The DP-BBSA are:

$$\int_a^b s_{O,ij}(\omega)d\omega,$$

where a and b specify the limits of the broad band and $s_{O,ij}(\omega)$ is the element i, j of the matrix $S_O(\omega)$.

In the patents cited, the DP for the AEP and AEKG are defined as the coefficients of a Karhunen-Loeve bases. These parameters are known as Factorial Analysis loadings.

In the patents cited, transformations of the DP are carried out to guarantee their gaussianity. In the description of this invention a generic transformed scalar DP will be denoted with the letter x=T(DP) and a vector with the notation x=T(DP), after the transformation $x \sim N_R^{2,p}(\mu_x, \Sigma_x)$.

In the patents cited, a comparison of the DP is carried out with respect to the normal variability (inferred from normative databases) by means of the univariate z transform that expresses the DP as a deviation measured in units of standard deviation $\sigma_x$, with respect to the populational average $\mu_x$. In the calculation of the $z_x$ based on the normative database, the effect of concomitant variables that originate variability that is not of diagnostic interest (as is the case of the subject's age), is eliminated by means of homoscedastic polynomial regression.

In the construction of brain and heart Topographic Maps (TM), the degree of deviation of the subject with respect to the norm is coded by means of a color scale. The TM is an image interpolated between the measurements of the sensors, which represents a schematic two-dimensional projection of the head or of the torso.

Cluster analysis is used to define groups of similar subjects according to the values of their DP (see U.S. Pat. No. 5,083,571).

Linear discriminant analysis is used to classify a subject examined as belonging to a test group or a test group previously defined by cluster analysis on the basis of pre-defined values of their DP (see U.S. Pat. No. 5,083,571).

The measurement of the statistical distances of a subject with respect to his own previous states is carried out at selected moments. This offers information on the subject's physiological state, for example, in the following conditions: during an operation, while in intensive therapy, or while in evaluation for the evolution of pathology (U.S. Pat. Nos. 4,545,388; 4,447,270; 4,815,474; 4,844,086 and 4,841,983).

The utility of these methods has been confirmed in several studies (John, E. R.; Harmony, T. Valdés-Sosa and, P. (1987b): The uses of statistics in electrophysiology. In: Gevins, A. S. and Rémond, A. (Eds), Handbook of Electroencephalography and Clinical Neurophisiology. Revised Series. Volume 1, Elsevier, The Netherlands, 497–540 and John, E. R.; Prichep, L. S. and Easton, P. (1987a): Normative data bases and neurometrics. Basic concepts, methods and results of norm construction. In: Gevins, A. S. and Rémond, A. (Eds), Handbook of Electroencephalography and Clinical Neurophisiology. Revised Series. Volume 1, Elsevier, The Netherlands, 449–496).

However, these methods have the following limitations:

The DP-BBSA are insufficient as descriptive parameters for the quantification of many types of activities of the EEG. This is due to the loss of resolution caused by the averaging over bands in frequency, with the resulting loss of sensitivity and specificity in diagnoses (Szava, S.; Valdés, P.; Biscay, R.; Galán, L.; Bosch, J.; Clark, I. and Jiménez, J. C.: High Resolution Quantitative EEG Analysis. Brain Topography, Vol. 6, Nr. 3, 1994, pp. 211–219).

The analysis of a group of DP by use of TM is hindered by the high correlation among the variables. To overcome this difficulty, Galán et al. (Galán, L.; Biscay, R.; Valdés, P.; Neira, L. and Virués T. (1994): Multivariate Statistical Brain Electromagnetic Mapping. Brain Topography, vol 7. No.1) introduced the Multivariate TM by means of the use of the multivariate Z transform.

The evaluation of the normality of the TM is carried out by means of univariate statistics without taking into account the need for the control of Type I errors caused by the multiple comparisons for all point of the map. This increases to uncontrollable levels the probability of false anomaly detection.

The procedure for the statistical classification of subjects is based on the assumption that $x \sim N_R^{2 \cdot p}(\mu_x, \Sigma_x)$. This implies that the decision frontiers between the groups are linear which is too restrictive. In addition, optimal procedures for the selection of the DPs with highest classification power have not been applied.

The use of magnetic measurements b(t) are not included, in spite of the fact that these add additional information to that provided by v(t).

The analysis of physiological information is limited to v(t), without there being any inference about j(t). Therefore, none of these methods constitutes a modality of TPEC. They are merely an analysis of projections of j(t) on the surface of the body after being distorted by the tissues of the subject interposed between the generators of the neural/cardiac PEC and the sensors. In fact, the relationship between the PEC and the EEG/MEG/EKG/MKG depends on the conductor properties of the head and the torso (e.g. geometry, conductivity, electric and magnetic permeability, etc.).

Cerebral and Heart Multivariate Statistical Maps

Some of these limitations were overcome by the U.S. Pat. No. 5,282,474 of Pedro Valdés-Sosa et al. In this patent the use of statistical methods is claimed for the evaluation of the abnormal activity of the brain and of the heart with the following innovations:

(1) b(t) is added as an optional source of physiological information.

(2) Additional components of the time series s(t) are included in the form of markers of external events of more general type such as can be derived from the subject's own voluntary or involuntary reactions, or those obtained by the analysis of their own o(t). The series derived by such a pre-processing are the Event Related Components (ERC) derived from o(t).

(3) Expansion of the ERC in tensor products of functional space-time bases. These include not only the basis of Fourier, but also wavelets (for the description of non-stationary processes) among other sets of DP that increase flexibility in the description of physiological processes.

(4) Summarize inclusive of these DP by means of the use of higher order statistical moments and different parametric time series models. In particular the coefficients of linear autorregresive are included.

(5) The introduction as DP of High Resolution Spectral Analysis (HRSA) consistent in the use of $S_O(\omega)$ for all the frequencies $\omega$ according to the one transformed of discrete Fourier; and (6) The introduction in the TM of color scales based on the empirical probability distribution of the global maxima and global minima of the DP. This scale exercises an effective control of the probability of false pathology detection.

The improvements for the evaluation of brain activity introduced in the Sosa et al. '474 patent were exemplified as follows:

(1) By means of the construction of norms of HRSA for the Cuban population from 5 to 97 years (Valdés, P.; Biscay, R.; Galán, L.; Bosch, J.; Szava, S.; and Virues, T.: High Resolution Spectral EEG norms for topography. Brain Topography, 1990, vol. 3, pp. 281–282 and Valdés, P.; Bosch, J.; Serious of it Banks, R.; Hernández, J. L.; Pascual, R. and Biscay, R.: Frequency domain models for the EEG. Brain Topography, 1992a, vol. 4, pp. 309–319); and (2) By the showing that the DP-HRSA achieve a higher sensitivity and specificity than the DP-BBSA for the detection of neurological and psychiatric pathology (Szava, S.; Valdés, P.; Biscay, R.; Galán, L.; Bosch, J.; Clark, I. and Jiménez, J. C.: High Resolution Quantitative EEG Analysis. Brain Topography, Vol. 6, Nr. 3, 1994, pp. 211–219).

However, the construction of DP of o(t) used in the Sosa et al. '474 patent is limited to such parametric models as the DP-HRSA. These are only a complete description of o(t) for stationary and linear stochastic signals or those signals with limited types of nonlinearity. The inadequacy of such DP for the study of the EEG of some types of patient (i.e., those with epilepsy) was demonstrated by Hernández, Valdés-Sosa and Vila (Hernández, J, L., Valdés, P. A., and Vila, P. (1996) EEG spike and wave modeled by to stochastic limit cycle. NeuroReport, 7: 2246–2250).

Moreover, qEEG methods and qEKG are not applied to estimates of j(t). For this reason, they are not true variants of TPEC.

Tomography of Cerebral and Heart Primary Electric Currents

As in all type of Tomography, the starting point for the development of the TPEC is the establishment of a model that relates the observed data with the quantity to estimate, this model is known as the Direct Problem. In the TPEC, the direct problem postulates how the o(t) are generated the from j(t). This model has two components:

(1) The specific model of Volume Conductor assumed, that is to say, of the conductive properties of the head and the torso, in particular their geometry, conductivity, electric and magnetic permeability, etc; and (2) The model that is assumed for j(t), or source model; and The properties of the Volume Conductor are summarized in the electric $k^E(r)$ and magnetic $k^M(r)$ Lead Fields (LF). These are the kernels of Fredholm integral equations of the first kind that establish direct relationships between the PEC $j_P(r,t)$ with $V_{er}(t)$ and $b_{cn}(t)$.

$$V_{er}(t) = \int_{\Omega_v} k^E(r) \cdot j_P(r, t) dr^3 \quad (1)$$

$$b_{cn}(t) = \int_{\Omega_v} k^M(r) \cdot j_P(r, t) dr^3 \quad (2)$$

The discretization of the terms expressed in equations (1) and (2) lead to the following formulation of the direct problem:

$$o(t)=K \cdot j(t)+e(t) \quad (3)$$

where K is the discretized LF and $e(t) \sim N_t^{k,p}(0, \Sigma_{EE})$, being the error introduced at the sensors in the moment of the measurement.

The use of the LFs to formulate the Direct Problem instead of using the classic Green formulation results in remarkable advantages according to Rush and Driscoll (Rush S. and Driscoll D. A. EEG electrode sensitivity—an application of reciprocity. IEEE Trans. on Biomed. Eng., vol. BME-16, pp. 15–22, 1969) and Plonsey (Plonsey R. Capability and limitations of electrocardiography and magnetocardiography. IEEE Trans. Biomed. Eng., vol. BME-19, not. 3, pp. 239–244, 1972). This is mainly because all the conductive properties of the head or the thorax can be summarized in these magnitudes without assuming a specific model for the PEC.

However, it is well-known that the conductivity in the body is non homogeneous and non isotropic (Hoeltzell P. B. and Dykes R. W. Conductivity in the somatosensory cortex of the cat. Evidence for cortical anisotropy. Brain Research, 117, pp. 61–82, 1979), a fact that complicates the calculation of the LFs considerably. Nevertheless, a substantial simplification is possible when the conductivity is considered constant and isotropic in each tissue type, which constitute a compartment (Schwan H. P. and Kay C. F., The conductivity of living tissues. Ann. N.Y. Acad. Sci., vol. 65, pp. 1007–1013, 1957). This model of Volume Conductor is denominated Isotropic and Piecewise Homogeneous Volume Conductor (IPHC). In general, two types of model IPHC are in use for the head or the torso:

(1) Spherical: the simplest model that specifies that the surfaces defining the different compartments are concentric spheres. For this model explicit formula exist to evaluate K. This model is easy to evaluate but not very exact, mainly for the temporal regions of the head; and (2) Realistic: in which the surfaces of the compartments are obtained from an anatomical atlas. For this model numeric methods have been developed by Fletcher et al. (Fletcher D. J., Amir A., Jewett D. L. and Fein G. Improve method for the calculation of potentials in a realistic head shape model. IEEE Trans. Biomed. Eng., vol 42, not. 11, pp. 1094–1104, 1995) and Oostendorp and van Oosteroom (Oostendorp T. and van Oosterom A. The potential distribution generated by surface electrodes in homogeneous volume conductive of arbitrary shape. IEEE Trans. Biomed. Eng., vol. BME-38, pp. 409–417, 1991). However, this procedures is based on a boundary element method (BEM) for the calculation of the potential difference on the surfaces that limit the compartments produced by energizing the sensors.

The expression:

$$R_O=\|o(t)-K \cdot j(t)\|_{\Sigma_{EE}}^{p_O} \quad (4)$$

is the functional of the Direct Problem in the norm $p_O$. $l(o(t)|t), \Sigma_{EE})=C_O \exp[-R_o]$ is defined as the likelihood corresponding to equation (3), being $C_O$ the constant of normalization of the density. In what follows, unless otherwise stated, $p_O=2$.

The central objective of the TPEC is the estimation of j(t) by means of the minimization of $R_O=\|o(t)-K \cdot j(t)\|_{\Sigma_{EE}}^{p_O}$, which is the "Inverse Problem". It is well known that $RO=\|o(t)-K \cdot j(t)\|_{\Sigma_{EE}}^{p_O}$ lacks, in general, a unique solution since the LF operator has a non-trivial null space, even when simultaneous electric and magnetic measurements are available.

Estimation of the PEC is possible only if a priori information is contributed in the form of a model for j(t) that impose a series of restrictions. These may be classified as:

Extrinsic: consisting of requiring the compatibility of the desired solution with information provided from other types of neuroimages. About the cerebral anatomical neuroimages, typical requirements are: (1) that j(t) be estimated only inside the spherical Volume Conductor that models the head; and (2) that j(t) be restricted to the cortical surface of the of the subject with an orientation perpendicular to said cortex (Dale, A. M., and Sereno and, M. I., J. Cognit. Neurosc., 1993, 5:2, pp. 162–176).

Intrinsic: consisting of requirements about the shape and extent of areas of activated tissue. It is required that the activated areas are as small as possible while maintaining compatibility of the model with the data (simplicity). As for the variation in the shape in the space, j(t), this requirement has ranged from minimal smoothness (collections of Dirac deltas corresponding to current dipoles) to functions that are maximally smooth.

All the above stated conditions are imposed on the solution in two equivalent ways:

Regularization: Adding to $R_O=\|o(t)-K \cdot j(t)\|_{\Sigma_{EE}}^{p_O}$ a non-negative functional $R_J=R_J(j(t)|\Theta)$ and minimizing $R_O+\lambda \cdot R_J(j(t)|\Theta)$.

Bayesian estimation: Maximizing the a posteriori distribution $$P(j(t), \Sigma_{EE}|o(t)) \propto l(o(t)|j(t), \Sigma_{EE}) \cdot \pi(j(t)|\Theta) \quad (6)$$

where $\pi(j(t)|\Theta)=C_J \exp[-R_J]$ is the a priori probability of j(t).

The fundamental differences in the different methods that have been developed to estimate the generators of o(t) are in the model specified for j(t). These are reviewed as follows:

When $R_J(j(t)|\Theta)$ is a functional that guarantees that $N_g<\Theta_o$, where $\Theta_o$ is a constant that assures the uniqueness of the solution of $R_O=\|o(t)-K\cdot j(t)\|_{\Sigma_{EE}}^{PO}$. This class of models for j(t) is denominated current dipoles (Scherg, M. and Ebersole, J. S. (1993): Models of Brain Sources. Brain Topography. Vol. 5, Nr. 4, pp. 419–423).

$$j(r, t) = \sum_{g=1}^{N_g} \alpha_g(t) \cdot \mu_g(t)\delta(r - r_g) \quad (7)$$

Where $\alpha_g(t)$ is the activity of the generator g and $\mu_g(t)$ its orientation. A model of this type was described in the U.S. Pat. Nos. 4,949,725; 5,285,385; 5,524,086, and 5,361,774. The advantages of these models are: (1) they are effective for modeling situations in which a small group of regions is producing PEC, all of small extent, (2) the formulation leads to simple least squares estimation methods, (3) the set of resulting DP of the estimates is very compact, comprising the positions and orientations of each current dipole, and (4) due to the simplicity of the model, it is easy to include additional restrictions to the estimation of this model of PEC (Scherg, M. and Ebersole, J. S. (1993): Models of Brain Sources. Brain Topography. Vol. 5, Nr. 4, pp. 419–423). For example a certain degree of smoothness may be imposed on $\alpha_g(t)$ and the requirement that, $\mu_g(t)=\mu_g$ does not depend on time. These requirements stabilize the estimated DP.

Nevertheless, the dipolar models discussed have the following limitations:

(1) When the number of possible generators of PEC ($N_g$) becomes too large, this type of model requires of an excessive manual intervention of the operator. For this case, the inverse problem becomes again ill determined. In fact, these models do not include a statistical approach for determining $N_g$.

(2) When the different regions of tissue that generate PEC are distributed in extensive areas, the dipolar model estimates an equivalent dipole located at the center of mass of the actual region, and therefore produces an artifact (3) The smoothness of $\alpha_g(t)$ has been imposed by use of a spline basis, that limits its possible forms of the amplitude of the activity to belong to a Sobolev functional Space $W^2(L^2)$, (second derivative integrable Lebesgue).

This type of model has been used solely to describe the AEP or AEKG.

This model for generators has been applied using spherical and realistic models of the Volume Conductor. However, the LF methodology has not been used, which necessitates the use of numerical algorithms for the realistic case that are not very practical since they require the evaluation of a step of the BEM in each iteration.

A TPEC was proposed for the first time in the U.S. Pat. No. 5,307,807 of Valdés-Sosa et al., providing a new modality of medical image. This invention consists on a method and system to create three-dimensional maps of the amplitude, orientation and connectivity of the generators of neural/cardiac PEC with the following innovations:

(1) An estimate of j(t) on a three-dimensional lattice inside the body is carried out.

(2) DPs of the PEC of the CRE is considered.

(3) The information available from other types of Structural Medical Images is used to specify the conductive properties of the subject's body. It is also used to define the spatial extent of a lattice for which PEC are defined (thus limiting the possible sites where the PEC are to be estimated) and to determine the orientation of the PEC. The subject's corporal geometric characteristics are incorporated in the TPEC in a quantitative manner with the use of parametric models.

(4) The use of information on the metabolism of the subject under study, available from other types of functional medical images, in order to limit even further the lattice on which j(t) is to be estimated.

(5) The generators that are modeled include not only discrete sources (dipoles) but also diffuse generators that desribe background generator noise, in occasions of higher amplitude than the discrete generators.

(6) Frequency domain estimation is introduced for the generators of CRE, in particular the cross-spectral matrix, $S_j(\omega)$, of the generators is introduced.

The improvements for the evaluation of brain activity introduced in the Valdés-Sosa et al. '807 patent were later verified by studies on the origin of abnormal electric activities in patient with focal neurological lesions. See for example Harmony, T.; Fernández-Bouzas, A.; Marosi, E.; Fernández, T.; Valdés, P.; Bosch, J.; Riera, J.; Rodriguez, M.; Reyes, A.; Silva, J; Alonso, M. and Sánchez, J. M. (1995): Frequency Source Analysis in Patients with Brain Lesions. Brain Topography, vol 8. No.2.

However, the clinical works mentioned previously and others (Valdés, P.; Carballo, J. A.; Alvarez, A.; Diaz, G. F.; Biscay, R.; Pérez, M. C.; Szava, S.; Virués, T. and Quesada, M. E.: qEEG in to public Health System. Brain Topography, Vol. 4, Nr. 4, 1992b, pp. 259–266) showed that the inventions described in the patents U.S. Pat. No. 5,282,474 and U.S. Pat. No. 5,307,807 did not take into consideration the following aspects, necessary for a more complete methodological elaboration of the TPEC:

(1) The statistical procedures described in the U.S. Pat. No. 5,282,474 were not extended for use in the TPEC. In particular, the sample space of the TPEC is a stochastic field defined on a 4 dimensions space time manifold, thus requiring for its analysis specific methods which were not taken into consideration in said patent.

(2) The regression methods used in the U.S. Pat. No. 5,282,474 to eliminate the effect of experimental concomitant variables are of a parametric global polynomial type. These are not sufficiently flexible for the description of the variations at multiple scales typical for electrophysiological data.

(3) In the case of the Valdés-Sosa et al. '807 patent, the only regularization resource consists of the control of the number of dipoles whose parameters are considered. This is an implicit use of the functional $R_J(j(t)|\Theta)$ that guarantees that $N_g<\Theta_o$, which is not very flexible and requires excessive human intervention.

(4) The solution for the direct problem that relates the activity of the generators with the observable signals is achieved with anatomical deconvolution. This method does not adapt to general configurations of generators and is only an inexact numeric approximation to the optimal solution.

(5) The parametric description employed to characterize the geometry of the subject's body is based on the use of quantitative descriptors of a functional form that are not sufficiently flexible to adequately describe inter-individual morphometric variability. In particular this method does not allow the inclusion of probabilistic anatomical information in those cases for which the acquisition of structural images of the particular subject under study is either undesirable or impracticable.

(6) The metabolic information available from other image modalities is only integrated as a restriction to the regions in which active dipoles will be allowed. Thus this information is not used in a statistically optimal estimation procedure.

Since the publication of the two aforementioned patents, a series of works have appeared, that while not totally solving the problems outlined above, have contributed to the elaboration of the solutions that are claimed in the present invention. The relevant developments are enumerated next, accompanied by an evaluation of their advantages and inadequacies.

The DPs used in the construction of all the TPEC until the moment are either the raw data or sufficient statistics, derived from the data, almost always some of the lower order statistical moments in the time or frequency domain. Recent works (Hernández, J, L., Valdés, P. A., and Vila, P. (1996) EEG spike and wave modeled by to stochastic limit cycle. NeuroReport, 7: 2246–2250) demonstrate the need for flexible non-parametric descriptions for the temporal sequence of the EEG/MEG/EKG/MKG that allow the description of the dynamic activity, essentially nonlinear, that is characteristic of masses of neural and heart tissue.

The formula $R_j(j(t)|\Theta)=\|j(t)\|_{\Sigma_{EE}}^{p_j}$ includes classical regularization, which allows models of $j(t)$ in which the activated areas can be extensive and with smooth contours. In particular Linear Distributed Solutions are limited to estimate $j(t)$ for each time t separately. They assume that $R(t) \sim N_R^{k, p_o}(0, \Sigma_{EE})$ and that $j(t) \sim N_R^{k, p_j}(0, \Sigma_j)$ with $p_O$ and $p_j=2$. In consequence, the estimator of generic TPEC is formulated as a Spline type solution (Riera, J. J., Aubert, E., Valdés, P., Casanova, R. and Lins, O. Discrete Spline Electric-Magnetic Tomography (DSPET) based on Realistic Neuroanatomy. To appear in the proceedings of The Tenth International Conference on Biomagnetism, BIOMAG '96, Santa Fe, N. Mex., February 1996) where the smoothness of the solution is specified by the matrix $\Sigma_{JJ}$. The estimator of the PEC has, in this case, an explicit expression that is:

$$j(t)=\Sigma_{JJ} \cdot K^t \cdot (K \cdot \Sigma_{JJ} \cdot K^t + \Sigma_{EE})^{-1} \cdot v(t) \qquad (8)$$

The most significant representatives in this family of TPEC are characterized by assuming that $\Sigma_{EE}=\sigma^2_{EE} I$, where $\sigma^2_{EE}$ is a variance common to the sensors of the same type. The different linear solutions are characterized by the $\Sigma_j$ postulated as indicated below.

Minimum Norm TPEC (MN) for which $\Sigma_J=\sigma_J^2 \cdot I_{3 \cdot N_g}$. This solution requires that the configuration of generators has minimum energy (Wang J. Z., Williamson S. J. and Kaufman L. Magnetic source images determined by lead-field analysis: the unique minimum-norm least squares estimation. IEEE Trans. Biomed. Eng., 39, 7, 665–667, 1992) compatible with the likelihood. This method produces spatially widespread estimates that do not localize discrete sources correctly. Variants of this methodology were presented in the U.S. Pat. No. 5,228,443.

Weighed Minimum Norm TPEC (WMN), $\Sigma_J=\sigma_J^2 \cdot W^{-2} \otimes I_3$, where the matrix $W=\mathrm{diag}(w_i)$ $$w_i = \sqrt{\sum_{d=1}^{N_d} |K|^2_{\bullet, d}}$$

W is diagonal and it contains weights. These counteract a bias that distributed solutions have of concentrating solutions near the sensors (George, J. S, P. S Lewis, H. A Schlitt, L. Kaplan, I. and C. C Wood (1993) Strategies for source space limitation in tomographic inverse procedures. In: Proc. 9th Int. Conf. On Biomagnetism, Vienna). It has been demonstrated that this method avoids spurious superficial solutions but it does not localize discrete sources with more precision.

Low resolution electric Tomography (LORETA) where:

$$\Sigma_J=\sigma_J^2 \cdot (\Lambda_m \cdot L^2 \cdot \Lambda_m)^{-1} \otimes I_3$$

$\Lambda_m=W$, $L_3=L \otimes I_3$, L being the matrix of the discretized Laplacian. This solution imposes the maximum spatial smoothness compatible with the likelihood term (Pascual-Marqui, R. D., 1994. Low resolution electromagnetic tomography: a new method for localizing electrical activity in the brain, Int. J. Psychophysiol. 18:49–65. LORETA). This method localizes a single point source accurately in any part of the brain or heart. LORETA has been extended for the estimation of the cross-spectrum of the generators of the EEG. (see Casanova, R., Valdés P., Garcia F. M., Aubert E., Riera, J. J., Korin W. and Lins O. Frequency domain distributed inverse solutions. To appear in the proceedings of The Tenth International Conference on Biomagnetism, BIOMAG '96, Santa Fe, N. Mex., February 1996). This is based on the following estimator:

$$S_J^{1/2}(\omega)=\Sigma_J \cdot K^t \cdot (K \cdot \Sigma_J \cdot K^t + \Sigma_E)^{-1} \cdot S_v^{1/2} \qquad (9)$$

However, $S_J^{1/2}(\omega)=\Sigma_J \cdot K^t \cdot (K \cdot \Sigma_J \cdot K^t + \Sigma_E)^{-1} \cdot S_v^{1/2}$ does not correspond to a complete Bayesian model, since an a priori probability is specified for $j(t)$, but not for $\Sigma_j$.

In some cases, additional restrictions can be imposed to obtain the well-known Backus and Gilbert solution, as described in U.S. Pat. No. 4,977,896.

All these Spline methods specify the membership of $j(t)$ to a Sobolev Space $H^q(L^2)$, for integer q, which is too restrictive since the estimation of dipolar types of PEC are not allowed. In fact, the Raleigh limit is valid which states the impossibility of discriminating nearby point sources. This limit is the cause, additionally, of the appearance of "ghost" solutions that are interference artifacts due to the limited resolution of linear methods.

In search of less widespread solutions, several authors have proposed non-linear estimators of $j(t)$. Among these (1) Matsuura and Okabe (Matsuura K. and Okabe Y. (1995) Selective Minimum-Norm Solution of the Biomagnetic Inverse Problem. IEEE Trans. BME Vol. 43 not. 6 pp. 608–615) have varied of $p_o$ and $p_j$ in the Generalized gaussian distributions that define the inverse problem with the consequence that the inverse solution must now be estimated non-linearly; (2) Gorodnitsky and Bhaskar (Gorodnitsky, I. and Bhaskar D. R. 1997. Sparse signal reconstruction from limited data using FOCUSS: a reweighted minimum norm algorithm. IEEE Trans. Signal Proc. Vol. 45 (3) pp 600–616) have proposed to apply iteratively the estimator of $R_O+\lambda \cdot R_J(j(t)|\Theta)$ weighting each lattice point proportionally to the $j(t)$ value estimated in the previous step. Both proposals converge algorithmically to a number of discrete generators equal to the number of sensors, therefore being in effect a more elaborate form of dipole fit. In consequence, they share with these dipolar models the defect that they can not estimate spatially distributed sources.

Philips et al. (Philips J W, Leahy R M and Mosher J C. MEG based imaging of focal neuronal current sources.

(1997). IEEE trans Medical Imaging, Volume 16: 338–348) introduced for $P(j(t),\Sigma_{EE}|o(t)) \propto l(o(t)|j(t),\Sigma_{EE}) \cdot \pi(j(t)|\Theta)$ the functional $$R_j(j(t)|\Theta) = \|\psi(t)\|_{\Sigma_{\psi\psi}}^{p\psi} + V(z(t)) \quad (10)$$

where $j(t) = \psi(t) \cdot *(z(t) \otimes 1_3)$. This functional penalizes the lack of smoothness of $\Psi(t)$ in the metric of $\Sigma_{\psi\psi}$. It also imposes the additional requirement that there are few active $Z_i$ (which is controlled by the weights $\alpha_I$) which will be concentrated in neighborhoods $\xi_I$ (whose dispersion is controlled by means of the parameters Q and the weights $\beta_i$). This is accomplished by means of the term $$V(z(t)) = \sum_{i=1}^{N_g} \left\{ \alpha_i \cdot Z_i(t) + \beta_i \cdot \left[ \sum_{i \in \xi_i} (Z_i(t) - Z_i(t))^2 \right]^Q \right\}$$

The resulting Bayesian hierarchical model is estimated by using the method of "Mean Field Annealing." This model, although potentially very flexible it has only been described for the case $\Sigma_\psi = \sigma_\psi^2 \cdot W^{-2} \otimes I_3$.

None of the methods described above models the temporal dependencies of j(t), which is equal to the use of the implicit assumption that j(t) is independent for each t. This assumption can cause considerable bias in the statistical estimates.

It should be mentioned that numerous works carry out processing of o(t) images, sometimes taking into account information contributed by other neuroimage modalities, that however do not have as an objective the estimation and ulterior use of j(t). Such is the case of the patent from Finland 925,461 and the U.S. Pat. No. 5,331,970. Since these patents do not having as an objective the obtaining of a TPEC, these types of antecedents will not be included in this analysis of the art.

DESCRIPTION OF THE INVENTION

The object of the present invention is to provide a system and a method for calculating an estimate of j(t) based on o(t), said estimate being denoted as TPEC. When referring to the study of the brain, specifically Tomography of the Cerebral Primary Electric Current, the procedure will be denoted (TPECc); and in the case of the heart, as Tomography of the Heart Primary Electric Current, (TPECk).

The map is the inverse solution of the EEG/MEG/EKG/MKG problem based upon: (a) the restriction of the solution to structures with high probability of generating electric activity using for this restriction an Anatomical Atlas and (b) imposing that the solution belong to a pre-specified functional space, of Besov type or is defined by a Megadictionary. The probability is determined that this map, or a subset of the same, belongs to a test group. For this determination, the spatial and temporal correlations of the map are modeled as well as their dependence on experimental covariables. The resulting probabilities are coded in a pseudocolor scale and they are superimposed on an Anatomical Atlas for their interactive three-dimensional visualization. The Atlases used in the solution of the inverse problem and for visualization, can be individual Structural Neuroimages, Probabilistic Atlases, or plastic deformations from a Probabilistic Atlas to the morphology of an individual.

One of the aspects of the present invention consists then of a System for the Tomography of the Primary Electric Current (TPEC) of the brain (TPECc) and of the heart (TPECk) comprising the following elements:

a plurality of external sensors of electric and/or magnetic fields placed in the proximity of the subject's body which are connected to the amplification sub-system, in the case of TPECc said sensors being placed in the proximity of the subject's skull and in the case of TPECk said sensors being placed in the proximity of the subject's torso;

an amplification sub-system consisting of pre-amplifiers and electronic amplifiers that record the signals detected by said sensors and carry out the pre conditioning of said signals for their analog to digital conversion;

a sub-system of analog to digital conversion that transforms the amplified signals into a sequence of binary numbers o(t) and stores said sequence in the memory of a general-purpose digital computer that serves as a control unit (CU), in the case of the TPECc the time series obtained from the electric sensors is the Electroencephalogram (EEG) and the time series obtained from the magnetic sensors the magnetoencephalogram (MEG), while in the case of the TPECk, the time series obtained from the electric sensors is the electrocardiogram (EKG) and the time series obtained of the magnetic sensors the magneto-cardiogram (MKG);

a sub-system of external digital storage coupled to the CU that allows the input of an Anatomical Atlas of the brain or of the heart in a reference system of the head or the torso, respectively, as well as the conductance values, electric and magnetic permitivity associated to the tissues described in this atlas, a particular but not exclusive instance of reference system for the brain being the "Talairach" international system.

a sub-system of external digital storage coupled to the CU, where the CU allows the input of images of functional states of the brain or heart of a subject obtained by other biophysical procedures such as Functional Magnetic Resonance Imaging (fMRI), Positron Emission Tomography (PET) and Single Photon Emission Tomography Photons (SPECT), said functional images being defined in the reference system of the head or of the torso, the lattices of time instants being designated in this case by $\Im_3$, $\Im_4$, and $\Im_5$ for MRI, PET, and SPECT, respectively;

a device for detecting the position of sensors that emits in digital form, the coordinates of these sensors as well as the coordinates of external anatomical structures of the head or of the subject's torso, these coordinates are defined in the reference system of the head or the torso and they are stored in the CU;

a plurality of stimulating devices connected with the CU that emit auditory, visual sensorial stimuli, as well as heat, electric, and magnetic pulses for the purpose of stimulating the subject's nervous or cardiovascular system;

a plurality of sensor devices connected with the CU that measure the motor, physiological and verbal reactions of the subject under study;

a CU in whose memory a group of instructions, or program, resides for the control of the realization of studies, the field of action of this program being among other purposes, the activation of the stimulating devices according to a preset design, the control of the acquisition of the EEG/MEG/EKG/MKG, the determination of the positions of the sensors, the recording of the activity of the subject under study, the acquisition of the images coming from other biophysical modalities and the digital processing of all the information acquired in a study of a subject for the construction of three-dimensional statistical maps of the temporal evolution of the functional states of the brain or heart.

Additionally the present invention provides a calculation method that will be used in conjunction with the aforementioned system, and that it is comprises the following steps:

Conversion of the coordinates of the sensors to the reference system of the anatomical atlas (FIG. 4). This is achieved by means of the application of a visco-elastic deformation, (most generally, non linear) that puts into correspondence the coordinates of the external anatomical markers of the subject with the anatomical atlas stored in the CU.

Calculation of the linear operators (electric Kernel and magnetic Kernel) that predict the EEG/MEG/EKG/MKG that would be produced in the subject with the presence of PEC in any part of the brain or heart. This Kernel is calculated for the lattice $\Re_V$ using the electric or magnetic principle of reciprocity. This principle establishes a linear relationship between the electric and magnetic LFs with the electric field that appears when the sensors are energized with a direct or alternating current of low frequency, respectively. Therefore, this electric field summarizes all the conductive properties of the head or the thorax independent of the appearance of an arbitrary CEP. Theorem of Reciprocity: Let $\delta r^3$ be an element of volume inside the conductor $\Omega_V$. A point source of primary current $j_P(t)\delta r^3$ in the position $r_g$ inside the conductor is reflected as a difference of elementary potential $\delta V_{er}^g(t)$ in the electrode lead localized on the scalp; and as an elementary projection of the magnetic field $\delta b_{cn}^g(t)$ on the direction normal to an simple coil external to the head (FIG. 5). Under passive conditions (PEC equal to zero in the conductor), the two situations enunciated below will produce different distributions of electric field in the whole conductor. (1) For the EEG, a direct current $I_{er}$ (leaving the conductor by the recording electrode and entering by the reference) applied to the same lead electrode (FIG. 6a). The electric theorem of reciprocity establishes:

$$\frac{j_j(r_g) \cdot j_P(t)\delta r^3}{\sigma_j I_{er}} = -\delta V_{er}^g(t).$$

(2) For the MEG an alternating current $I_c(\omega)$ (at a specific frequency ($0 \leq \omega \leq 100$)Hz) circulating in the same coil (FIG. 6b). The theorem of reciprocity establishes:

$$\frac{j_j(r_g, \omega) \cdot j_P(t)\delta r^3}{i\omega\sigma_j I_c(\omega)\Delta S_c} = -\delta b_{cn}^g(t).$$

The calculation of the electric fields $j_j(r_g)$ and $j_j(r_g,\omega)$ in the two previously described situations should be computed in order to obtain the electric and magnetic LFs. This calculation can be carried out on the basis of a model of the realistic physical characteristics of the head or torso of the subject as a conductor. The use of the Finite Element Method (FEM) or Finite Difference (FDM) (Ramirez, S., Eisenberg, J. Lehr and F. Schoen. Effects of cardiac configuration, paddle placement, and paddle size on defibrillation current distribution: A finite element mode. Med. Biol. Eng. Comput., vol. 27, pp. 587–594, 1989; Fahy, J., Kim Y. and Ananthaswamy A. Optimal electrode configurations for external cardiac pacing and defibrillation: An inhomogeneous study. IEEE Trans. Biomed. Eng., vol. BEM-34, pp. 743–748, 1987), allows modeling a Volume Conductor which is inhomogeneous and anisotropic. For this case, $\Re_V$ consists of tetrahedrons. If the Volume Conductor is considered an IHPC, the Boundary Element Method is used (BEM) (Oostendorp T. and van Oosterom A. The potential distribution generated by surface electrodes in homogeneous volume conductive of arbitrary shape. IEEE Trans. Biomed. Eng., vol. BME-38, pp. 409–417, 1991). For this particular case tetrahedrons are also used to discretize the volume, but with the difference that these tetrahedrons, when intersecting the surfaces separating successive compartments, form triangles, these surfaces being discretized by means of a lattice. All these methods have been developed based on the formulation of a scalar boundary problem for the electric potential. These lead to an ill-posed problem (from the physical point of view) due to the uncertainty in determining the electric potential up to a spatial constant. Once the electric potential is calculated, then some type of numerical gradient is used to calculate the electric potential in the situations enunciated previously. The method proposed by Fletcher et al. (Fletcher D. J., Amir A., Jewett D. L., and Fein G. Improve method for calculation of potentials in to realistic head shape model. IEEE Trans. Biomed. Eng., vol 42, not. 11, pp. 1094–1104, 1995), denominated Lead Field Analysis (LFA), is also based on the solution of a BEM problem for the electric potential. The main difficulty of this methodology is that the matrices originated by all these methods are singular and therefore the use of a method of multiple deflations is needed to obtain a particular solution (Lynn M. S. and Timlake W. P. The uses of multiple deflations in the numerical solution of singular systems of equations, with application to potential theory. SIAM J. Numer. Anal., vol. 5, not. 2, 1968). In addition, when increasing or diminishing the ratio between the conductivity of the skin and of the bone, the resulting matrices become very ill conditioned. Numerical errors introduced by said ill conditioning have been reduced when using the formulation of the isolated problem Hamalainein and Sarvas (Hamailainen M. S. and Sarvas J. 1989. Realistic conductivity model of the head for interpretation of neuromagnetic dates. IEEE Trans. Biomed. Eng. Vol. 36, pp. 165–171). All these methods can be extended to the calculation of these electric fields under the formulation of a vector boundary problem for the ohmic current density originated in both situations, leading to vector versions of the FEM, FDM, and BEM. Contrary to the scalar versions the matrices that originate from discretization of the equations are not singular, the use of the method of multiple deflations being avoided this way. The "sparse" ill conditioning (when increasing or diminishing the ratios among the conductivities) is reflected in said matrices by the appearance of a block structure. It being possible for the vector version of BEM to calculate the inverses by blocks, something that is not possible in the scalar case since these inverses are not defined. As an example, the case of a vector BEM is developed in detail below.

The procedure originates systems of algebraic equations of a large scale. The use of multi-resolution analysis based on the principle of thresholding allow the conversion of these enormous algebraic systems of equations into a sparse format, allowing in this way a considerable reduction of the computational cost and of the errors introduced by rounding (D. M. Bond and S. A. Vavasis. Fast wavelet transforms for matrices arising from boundary element methods, 1994 and Glowinski R., Bread T. W., Wells R. O. and Zhou X. Wavelet and finite element solutions for Neumann problem using fictitious domains, 1994).

Determination of the Possible Sites of Presence of Generators of PEC in the Head or the Thorax by Means of the Use of an Anatomical Atlas.

In the particular case of an isotropic piecewise homogeneous volume conductor (IPHC), said IPHC consists of N compartments ($R_1, R_2, \ldots, R_N$) that do not intersect and are ordered so that said compartments contain each other. The air is, $R_{N+1}$ by definition. Additionally, $\sigma_j$, represents the value of the conductivity in the compartment $R_j$, ($\sigma_{N+1}=0$). The surface $S_{j,j+1}$ is the frontier that separates the compartments $R_j$ and $R_{j+1}$. The vector $n_j(r)$ denotes the normal r to the surface in the position (FIG. 7)

Volume Conductor and Generating Lattices

Selecting an anatomical image and specifying the Cartesian coordinates, in the common reference system, of its constituent voxels as the lattice of the volume conductor $\mathfrak{R}_v$. For each point $r_v$ of $\mathfrak{R}_v$, the probability $p(s,r_v)$ of that voxel belonging to a given tissue type s, thus defining an anatomical atlas, is specified. Labeling each point $r_v$ of the lattice of the volume conductor with the tissue type that has the highest probability, that is $s_v=\arg \max_v(p(s,r_v))$.

For each point $r_v$ of the lattice of the volume conductor $\mathfrak{R}_v$, the conductivity value corresponding to the tissue label $s_v$ is also specified, said value being taken from a predefined set of conductivities, designated as the conductivity profile $\sigma$.

Selecting the label b that indicates excitable tissue (gray matter in the brain or myocardium in the heart) in order to define the probability $p(b,r_v)$ of excitable tissue for each point $r_v$.

The set $\mathfrak{R}_g$ of $N_g$ points $r_g$ for which the probability is non-zero. The probability function $p_g=p(b,r_g)$ being defined on $\mathfrak{R}_g$.

Computation of the Electric and Magnetic Lead Fields

To specify the electric $k_{eg}$ and $k_{cg}$ magnetic lead fields, the ohmic current density $j_j(r)$ and $j_j(r,\omega)$ that appear from energizing the sensor, as described above, must be computed. The electric and magnetic lead fields in the j-th compartment can be computed by using the following expressions:

$$k_{eg} = -\frac{j_j(r_g)}{\sigma_j I_{er}}$$

at the lead electrode "er", and $$k_{eg} = -\frac{j_j(r_g, \omega)}{i\omega\sigma_j I_c(\omega)\Delta S_c}$$

at the coil "co," respectively. The lead fields are both evaluated at the point $r_g$ of the lattice of the generating volume $\mathfrak{R}_g$.

In the particular case of an isotropic piecewise homogeneous volume conductor (IPHC), the IPHC consists of N compartments ($R_1, R_2, \ldots, RN$) that do not intersect are are ordered so that the compartments contain each other. The air is $R_{N+1}$ by definition. Additionally, $\sigma_j$ represents the value of the conductivity in the compartment $R_j(\sigma_{N+1}=0)$. The conductivity profile is defined by $\sigma=(\sigma_j, j=1, \ldots, N)$. The surface $S_{j,j+1}$ is the frontier that separates the compartments $R_j$ and $R_{j+1}$. The vector $n_j(r)$ denotes the normal r to the surface in the position (FIG. 7).

1) The ohmic current density, $j_j(r)$, in each compartment $R_j$ for the situation (1) corresponds to a vector boundary problem and it can be calculated on the basis of the second Green vector formula:

$$4\pi j_j(r) = 4\pi j_\infty(r) + \sum_{k=1}^{N} \frac{(\sigma_k - \sigma_{k+1})}{\sigma_k} \oint_{S_{k,k+1}} (\nabla' \times G(r,r')) \cdot (n_k(r) \times j_k(r')) d\,r'^2 \quad (11)$$

$$\text{where:} \quad j_\infty(r) = -\frac{I_{er}}{4\pi} \nabla \cdot (G(r, r_e) - G(r, r_r)) \quad (12)$$

2) The ohmic current density, $j_j(r)$, in each compartment $R_j$ for the situation (2) also corresponds to a vector boundary problem and can be calculated directly on the basis of the second Green vector formula:

$$4\pi j_j(r, \omega) = 4\pi j_\infty(r, \omega) + \sum_{k=1}^{N} \frac{(\sigma_k - \sigma_{k+1})}{\sigma_k} \oint_{S_{k,k+1}} (\nabla' \times G(r,r')) \cdot (n_k(r) \times j_k(r', \omega)) d\,r'^2 \quad (13)$$

$$\text{where:} \quad j_\infty(r, \omega) = \quad (14)$$

$$\frac{i\omega}{4\pi}\sum_{k=1}^{N} (\sigma_k - \sigma_{k+1}) \oint_{S_{k,k+1}} G(r, r') \cdot (n_k(r') \times b_c(r', \omega)) d\,r'^2$$

In addition, the vector magnetic field density produced by a coil in an infinite and homogeneous medium is calculated according to the expression:

$$b_c(r, \omega) = \frac{\mu_o I_c(\omega)\Delta S_c}{4\pi} \nabla \times \nabla \times (G(r, r_c) \cdot n_c) \quad (15)$$

Equations (11) and (13) are solved analytically if the symmetry of the IPHC allows a representation in a system of curvilinear coordinates that allows a separation of variables for the solution of the Laplace vector equation. Otherwise, these they should be transformed to Cartesian coordinates and discretized. Notice that for a fixed frequency $\omega=\omega_c$ in (13) these equations only differ in the independent term $\{j_4(r),j_\infty(r,\omega_c)\}$. Let us denote the general vector field as $c_k(r)=\{j_k(r),j_k(r,\omega_c)\}$. One can then write that for an independent term $c_\infty(r)$ this general vector field satisfies the equation:

$$c_j(r) = c_\infty(r) - \sum_{k=1}^{N} \frac{(\sigma_k - \sigma_{k+1})}{\sigma_k} q_k(r) \quad (16)$$

Where: $q_k(r) = -\frac{1}{4\pi} \oint_{S_{k,k+1}} (\nabla' g(r,r')) \times (n_k(r') \times c_k(r')) d r'^2$ A vector BEM based on this equation obtains when the limit $r \to S_{j,j+1}$ is calculated and when the resulting Fredholm integral equation of second type is discretized. This leads to a set of algebraic linear equations:

$$Dc = c_\alpha - \Gamma c \quad (17)$$

Where $c_\psi = (C_{1\alpha}; \ldots; c_{N\alpha})$, $c = (c_1; \ldots; c_N)$, and the matrices:

$$\Gamma = \frac{1}{4\pi} \begin{pmatrix} \frac{(\sigma_1 - \sigma_2)}{\sigma} \Gamma_{11} & \frac{(\sigma_2 - \sigma_3)}{2} \Gamma_{12} & \ldots & \Gamma_{1N} \\ \frac{(\sigma_1 - \sigma_2)}{\sigma_1} \Gamma_{21} & \frac{(\sigma_2 - \sigma_3)}{\sigma_2} \Gamma_{22} & \ldots & \Gamma_{2N} \\ \vdots & \vdots & \ddots & \vdots \\ \frac{(\sigma_1 - \sigma_2)}{\sigma_1} \Gamma_{N1} & \frac{(\sigma_2 - \sigma_3)}{\sigma_2} \Gamma_{N2} & \ldots & \Gamma_{NN} \end{pmatrix}$$

$$D = \begin{pmatrix} \alpha_1 I_{N_{1,2}} & 0 & \ldots & 0 \\ 0 & \ddots & 0 & \vdots \\ \vdots & 0 & \alpha_{N-1} I_{N_{N-1,N}} & 0 \\ 0 & \ldots & 0 & I_{N_{N,N+1}} \end{pmatrix}$$

The $(3N_{j,j+1} \times 1)$ vectors $c_{j\alpha}$ and $c_j$ are formed by the evaluation of $c_{j\alpha(r)\, and\, cj}(r)$ at the centers of mass of the triangles of the surface $S_{j,j+1}$. $c_k$ is a $(3N_{k,k+1} \times 1)$ vector built by the evaluation of in the centers of mass of the triangles of the surface $S_{k,k+1}$. The $(3N_{j,j+1} \times 3N_{k,k+1})$ matrix $\Gamma_{jk}$ contains the numerical evaluation of $\Gamma_n^k(r)$ at the centers of masses of the triangles of the surface $S_{j,j+1}$.

$$\Gamma_{jk} = \begin{pmatrix} \Gamma_1^k(r_1^j) & \ldots & \Gamma_{N_{k,k+1}}^k(r_1^j) \\ \vdots & \ddots & \vdots \\ \Gamma_1^k(r_{N_{j,j+1}}^j) & \ldots & \Gamma_{N_{k,k+1}}^k(r_{N_{j,j+1}}^j) \end{pmatrix}$$

Where $\Gamma_n^k(r) = \Omega_n^k(r) I_3 - (n_n^k \cdot \lambda_n^k(r))$:

The solution of the system of algebraic equations (17) is obtained inverting the matrix of the system: $c_{est} = (D + \Gamma)^{-1} c_\alpha$. This system of algebraic equations does not have problems of singularity since the ohmic current density does not depend on specifying any reference.

The value of $c_j(r)$ at an interior point r of the compartment $R_j$ is obtained by substituting, the general vector field estimated on the surfaces, into the following expression:

$$c_j(r) = c_\infty(r) - \frac{1}{4\pi} \sum_{k=1}^{N} \frac{(\sigma_k - \sigma_{k+1})}{\sigma_k} \sum_{n=1}^{N_{k,k+1}} \Gamma_n^k(r) c_{n_{est}}^k$$

Independent Terms EEG/MEG

For the EEG

Keeping in mind the fact that the current injected is considered constant over the triangles marked on the scalp, corresponding to the electrodes the following is obtained:

$$c_\infty(r) = \frac{I_{er}}{4\pi} \left( \frac{(r - r_e)}{|r - r_e|^3} - \frac{(r - r_r)}{|r - r_r|^3} \right)$$

For the MEG

If at the fixed frequency $\omega = \omega_c$ it is considered that the magnetic field vector density is constant on each triangle and equal to its value at the center of mass, we obtain:

$$c_\infty(\vec{r}) = j_\infty(r, \omega_c) = -\frac{i\omega_c}{4\pi} \sum_{k=1}^{N} (\sigma_k - \sigma_{k+1}) \sum_{n=1}^{N_{k,k+1}} n_n^k \times b_{cn}^k \eta_n^k(r)$$

where: $\eta_n^k(r) = \int_{\Delta_n^k} \frac{dr'^2}{|r - r'|}$

Note that it is necessary to specify the transversal component of the magnetic field vector density in each one of the triangles that form each surface. For this, it is only necessary to evaluate the expression mentioned below in each one of the centers of masses of the triangles.

$$b_{cn}^k = b_c(r_n^k, \omega_c) = \frac{\mu_o I_c(\omega_c) \Delta S_c}{4\pi} \left( \frac{3 n_c \cdot (r_n^k - r_c) \circ (r_n^k - r_c)}{|r_n^k - r_c|^5} - \frac{n_c}{|r_n^k - r_c|^3} \right)$$

Calculation of the Inverse Solution

The solution to the inverse problem is based on formulating a Hierarchical Bayesian model similar to those proposed in a different context for biomedical image fusion (Hurn M. A. et al., Bayesian Fused Classification of Medical Images, IEEE Trans. Medical Imaging (1996), Vol. 15, No. 6, pp. 850–858; Mardia K. V., Hainsworth T. J., Kirkbride J., Hurn M. A. and Barry C., Hierarchical Bayesian Classification of Multimodal Medical Images, Proc. Mathematical Methods in Biomedical Image Analysis, IEEE Computer Society Press (1996), pp. 53–63).

At the most basic level in the model the existence of a non-observable brain or heart tissue activation, A(t), is postulated.

All observed neuroimaging modalities are assumed to be generated by a common non-observable brain or heart tissue activation $a(r_g, t)$ that is defined for each point $r_g$ of the lattice of the generating volume $\Re_g$. The vector of activation for the whole generating volume will be denoted by $a(t) = [a(r_g, t)]_{r_g \in \Omega_g}$.

As a consequence of activation, different physiological changes occur, each of which will be quantified by means of the functional indicators $f_m(r_g, t)$, where m indexes the type of physiological change. The vector of the m-th functional indicators for the whole generating volume will be defined by $f_m(t) = [f_m(r_g, t)]_{r_g \in \Omega_g}$.

In turn, a functional indicator originates observations characteristic of a given neuroimaging modality. Each neuroimaging modality has its given spatial and temporal resolution. Particular (but non-exclusive) examples of functional indicators and their associated neuroimaging modalities are: the PEC in the case of the EEG where $f_1(r_g,t)=j_p(r_g,t)$ and MEG where $f_2(r_g,t)=j_p(r_g,t)$; the change in local concentration of deoxy-hemoglobin blood vessels measured by $f_3(r_g, t)=j_p(r_g,t)$ in the case of fMRI; the rate of glucose consumption measured by $f_4(r_g,t)=j_p(r_g,t)$ in the case of PET; etc.

The model comprises the following components:

Likelihood terms $I_{o_m}$ for each modality m based on the corresponding direct problem $$o_m(t)=(K_m*f_m)(t)+e_m(t) \quad (18)$$

$$(K_m*f_m)(t) = \sum_{t_l=\mathcal{J}} \sum_{r_g=\mathcal{R}_g} w_m(g,l) K_m(r_g,t,t_l) f_m(r_g,t_l),$$

of which simple local averaging is obtained by specifying $$w_m(g,l) = \frac{1}{N_g + N_t^m}.$$

Expression (18) relates each observation $o_m(t)$ with its associated functional indicator $f_m(t)$. This expresses that the image modality m is a smoothed version of the functional indicator with an additional additive instrumental error. The kernel $K_m$ of the smoothing operator models the actual amount of spatial and temporal smoothing inherent to each imaging modality. Thus, the bandwidth for temporal smoothing is very small for the EEG/MEG, which reflects high temporal resolution, while the bandwidth for spatial smoothing is high, which reflects low spatial resolution of this imaging modality. The converse is true for fMRI. The additive instrumental error is taken $e_m(t) \sim I_{o_m}(o_m(t) - K_m * f_m (t)|\Theta_{e_m})$, is also assumed. The notation $f=[f_m]_{1 \leq m \leq M}$ shall be used. Note that for the EEG and MEG, $f_m(t)=j(t)$.

a priori Probabilities, $\pi_{f_m}$, for each functional activity $f_m(t)$ to a degree of cerebral activation $a(t)$ according to the relationship $$f_m(t)=H_m \cdot A(t)+\beta_m(t) \quad (19)$$

that expresses the form in which $a(t)$ is projected according to some mechanism $H_m$ to produce the functional indicators. Random variations of the functional indicators, $\beta_m(t) \sim \pi_{f_m}(f_m(t)-(H_m \cdot a)(t)|\Theta_{\beta_m})$, are also assumed. The notation $\Theta_\beta=[\Theta_{\beta_m}]_{1 \leq m \leq M}$ and $\Theta_\Theta=[\Theta_{\Theta_m}]_{1 \leq m \leq M}$ will be used.

A priori probability $\pi_A$ of the brain or heart activation $a(t) \sim \pi_A(a(t)|\Theta_A)$.

A priori probabilities for the hyperparameters $$\Theta_a \sim \pi_{\Theta_a}(\Theta_a)$$

$$\Theta_{\beta m} \sim \pi_{\Theta_{\beta m}}(\Theta_{\beta m})$$

$$\Theta_{\gamma m} \sim \pi_{\Theta_{em}}(\Theta_{em})$$

All of which leads to the following basic a posteriori probability:

$$P(a(t), \Theta_a, f(t), \Theta_\beta, \Theta_e | o(t)) \propto \prod_{m=1}^{M} I_{o_m}(o_m(t) - (K_m * f_m) \quad (20)$$

$$(t) | \Theta_{\theta_m}) \times \prod_{m=1}^{M} \pi_{f_m}(f_m(t) -$$

-continued $$(H_m \cdot a)(t) | \Theta_{\beta_m}) \times \prod_{m=1}^{M}$$

$$\{\pi_{\theta_{\alpha_m}}(\Theta_{\theta_m}) \cdot \pi_{\theta_{\beta_m}}(\Theta_{\beta_m})\} \times$$

$$\pi_a(a(t) | \Theta_a) \times \pi_{\theta_a}(\Theta_a)$$

The notation $f(t)=[f_m(t)]_{1 \leq m \leq M}$ denotes the vector of all functional indicators. The estimation of all the parameters $a(t),\Theta_a,f(t),\Theta_\beta,\Theta_e$ of the model will be carried out by the Maximum method a Posteriori (MAP) method. For some embodiments of the invention, explicit estimators will exist. Otherwise the estimate will be obtained by one of the following iterative methods, taking as initial values those estimated of a simpler model or simply random values:

Iteratively modifying the parameters $a(t),\Theta_a,f(t),\Theta_\beta,\Theta_e$ until a maximum value of the a posteriori probability is achieved, said modification being carried out according to one of the following schemes:

Successive Maximization of $P(a(t),\Theta_a,f(t),\Theta_\beta,\Theta_e|o(t))$ Equation (20) for subsets of the parameters, while maintaining fixed all the others, "Iterated Conditional Maximization" (ICM; Winkler, G. (1995) Image Analysis, Random Fields and Dynamic Carlo Methods Mounts. Springer).

Successive Maximization of $P(a(t),\Theta_a,f(t),\Theta_\beta,\Theta_e|o(t))$ Equation (20) for subsets of the parameters., fixing the other parameters to their expected value, "Expectation Maximization" (EM; Tanner, 1996).

Choosing the mode of the Monte Carlo's distribution of $P(a(t),\Theta_a,f(t),\Theta_\beta,\Theta_e|o(t))$ obtained by means of Monte Carlo Markov Chain methods (MCMC, Tanner M. 1996 Tools for Statistical Inference. Third Edition. Springer).

The advantage of the formulation $P(a(t),\Theta_a,f(t),\Theta_\beta,\Theta_e|o(t))$ is that it allows the combination, in a statistically optimal manner, of information provided by imaging modalities with different temporal and spatial resolution. The weight that should be assigned to each modality is obtained in an automatic. In particular, it is possible to find the optimal relative weights with which the EEG and MEG should be combined. The form of the likelihood is specified by means of the form of the Risk $$R_{|\theta_{E_m}}[e_m|\Theta_{e_m}] = -\ln[I_{o_m}(e_m(t)|\Theta_{e_m})] + \ln[C_o] \quad (21)$$

The following notation is introduced for any set of variable x. Let the most important parameters of the distribution be the mean and the matrix of covariances $\Theta_x = \{\mu_x, \Sigma_x\}$. Then $$R_x^P[X|\Theta_x]_{\varepsilon,p} = \sum_{i=1}^{N_x} C_{\varepsilon,p}[z_i^x]$$

defines a polynomial risk of order p, ($\epsilon$ insensitive) with $$C[y]_{\varepsilon,p} = \begin{cases} 0 & |y| \le \varepsilon \\ \left|\dfrac{z^p}{p}\right| - \varepsilon & |y| > \varepsilon \end{cases} \qquad (22)$$

This class of risks includes the norms ($L_p$) of order p>1 used previously:

$$R_x^{L^p}[x \mid \Theta_x] = \|x - \mu_x\|_{\Sigma_x}^p = \sum_{i=1}^{N_x} C_{0,p}[z_i^x]. \qquad (23)$$

In addition, risks that are more general $$R_X^C[X \mid \Theta_X] = \sum_{i=1}^{N_x} C_{\varepsilon,p,\sigma}[Z_{i,\bullet}^X]$$

will be used
where $$C[w]_{\varepsilon,p,\sigma} = \qquad (24)$$

$$\begin{cases} 0 & |w| \le \varepsilon \\ c_{p,\sigma}(|w|-\varepsilon) & |w| > \varepsilon \end{cases} \text{ and } c_{p,\sigma}(z) = \begin{cases} \sigma^{1-p} \cdot \dfrac{z^p}{p} & z \le \sigma \\ z + \left(\dfrac{1}{p}-1\right)\sigma & z > \sigma \end{cases}$$

This type of risk includes many particular cases used in other contexts. When $\varepsilon=0$ and $p=2$ the risk correspond to that of Huber that defines robust estimators. The case $\varepsilon=0$ y$\sigma=0$ reduces to the norm $L_1$ mentioned previously. Finally, if $\sigma=0$ the norm is the $\varepsilon$ insensitive risk of Vapnik (1995).

In order to obtain the MAP estimator of $P(a(t),\Theta_a,f(t),\Theta_\beta,\Theta_e|o(t))$ using ICM, EM, or MCMC, an essential step is the minimization of expressions of the type $R_o + \lambda \cdot R_j(j(t)|\Theta)$ (Equation 5). We define $R_o$ as $R_x^P[x|\Theta_x]_{\varepsilon,p}$ or $R_x^C[x|\Theta_x]$ and $R_j(j(t)|\Theta)$ as $\|x-\mu_x\|_{\Sigma_x}^p$. The partial solution (Smola, 1966) is equivalent to regression with Support Vector Machines" (SVM). Besides allowing an efficient minimization, stated as a quadratic programming problem, also the solutions obtained are robust to data contaminated with outliers. Additionally the estimated PEC will be function of a reduced number of elements of $K_m$, which guarantees simplicity of the TPEC.

For both the EEG and MEG $f_m(t)=j(t)$, the PEC. The model for the PEC is further detailed as $$j(r_g,t) = \mu(r_g) \cdot a(r_g,t) + \xi(r_g,t) \qquad (25)$$

where $\mu(r_g):\Omega_g \to R^3$ is the field of orientations of the generators of the PEC, the activation $a(r_g,t):\Omega_g \times \Im \to R$ and $\xi(r^g,t):\Omega_g \times \Im \to R^3$ the additive random component $\beta_m(r_g,t)$ associated with j(t), said random component will be specified in a preferred embodiment as $\xi(r_g,t) \sim N_R^{3,2}(0,\sigma_\xi^2 \cdot I_3)$ without loss of generality. Equation (25) extends to the TPEC the spatio-temporal modeling initially introduced for cerebral dipoles (Equation 7; Scherg, 1993):

$$j(t) = M \cdot a(t) + \xi(t)$$

$$M = \begin{bmatrix} \mu_1 & 0 & \ldots & 0 & 0 \\ 0 & \mu_2 & \ldots & 0 & 0 \\ \ldots & \ldots & \mu_1 & \ldots & \ldots \\ 0 & 0 & \ldots & \mu_{N_g-1} & 0 \\ 0 & 0 & \ldots & 0 & \mu_{N_g} \end{bmatrix}, \quad \mu = \begin{bmatrix} \mu_1 \\ \mu_2 \\ \ldots \\ \mu_{N_g} \end{bmatrix}$$

where the $\mu_g$ are the orientations of the PEC for each point of $\mathfrak{R}_g$.

In this case, the a priori probability for the PEC takes the following specific form $\pi_{f_1}(f_1(t)-(H_1 \cdot a)(t)|\Theta_{\beta_1} = \pi_1(f_1(t)-Ma(t)|\Theta_1)\pi_2(\mu|\Theta_2)$. The a priori probability $\pi_2(\mu|\Theta_2)$ is calculated by either of the following expressions:

$\pi_2(\mu|\Theta_2) = \exp(-\|\Lambda_s \cdot \mu \Lambda_m\|_{B_{n,s}^m})$ where $\Lambda_s$ is a diagonal matrix that specifies the degree of smoothness that will be imposed at each point of $\mathfrak{R}_g$, and $\Lambda_m = W \cdot P$, where W is a prespecified weighting matrix and P is a diagonal matrix containing $p_g$ for all $r_g$; or by means of successive evaluation of the marginal distributions of $\pi_2(\mu|\Theta_2) = p_g \cdot N(0,\sigma_A^2) + (1-p_g) \cdot N(0,\sigma_B^2)$ with $N(0,\sigma^2)$ the univariate gaussian distribution with mean zero and standard deviation $\sigma$, where $\sigma_A^2$ and $\sigma_B^2$ being constants selected to be large and small, respectively, with respect to the expected variation of the orientations.

The a priori probability $\pi_1(f_1(t)-M \cdot a(t)|\Theta_1)$ for the functional indicator $f_1(t)$ is preferably defined as $\pi_{f_m}(f_m(t)-(H_m \cdot a)(t)|\Theta_{\beta_m}) = \exp(-C\|\Delta\|_{B_{n,s}^m})$ with the discrepancy vector $\Delta = f_m(t) - (H_m \cdot a)(t)$ and the norm $$\|\Delta\|_{B_{n,s}^m} \approx \sum_k a_k \cdot \|F_k\|^m$$

in $B_{n,s}^m$. C is a preselected constant. This result is due to the fact that $$\Delta = \sum_k F_k \cdot \Psi_k$$

where the $\Psi_k$ belong to a Dictionary of Atoms. Particular, but not exhausitve, examples of which are the Wavelet Dictionary, Fourier Dictionary, Dirac Delta Dictionary, or a mega-dictionary defined by the combination of several dictionaries.

In that the compatibility is demanded with the cerebral activation a(t), and a functional smoothness predefined by a Besov space, selecting a Besov Space in this case with index (1,1,s) leads to a Variable Resolution TPEC (VARETA). VARETA allows the estimation in the same framework of both point source generators, as well as distributed source generators, thus eliminating the absolute dichotomy between both types of modeling, existent up to now. In VARETA, the quantity of smoothness enforced in the solution is allowed to be variable from one point to another inside the generating volume (thereby the name "Variable Resolution"). This variable resolution allows spatially adaptive nonlinear estimates of the current sources that eliminate those "ghost" solutions present in the usual linear distributed solutions. It also allows the achievement of "super-resolution," which is the capacity to distinguish discrete sources very near one to the other. Note that the dependence on $p_g$ allows the probabilistic restriction of estimators for PEC to points of the lattice due to a priori knowledge. In particular, if $p_g$ only take the values 0 and 1, this restriction for the localization of the PEC becomes deterministic.

Statistical Evaluation

Determination of the Membership to a Test Group

Once the estimate of $j(x,t)$, $\gamma(x,t)$, and the hyperparameters are made for a given subject, a selection of these are composed in a vector of DP. This vector is used to determine if the TPEC obtained may be classified, using methods of non-parametric statistics (Ripley B. D. (1966) Pattern Recognition and Neural Networks. Cambridge University Press), in one of a multiplicity of test groups. Test groups that represent different embodiments of this invention are:

Groups of subjects defined as normal by means of criteria external to their TPEC. These groups will be specified implicitly by means of a sample of DP of TPEC of normal subjects contained in a database. The objective of the statistical analysis in this case, is to determine the probability that the DP of the TPEC evaluated is obtained from a healthy subject.

Groups of subjects defined as having pathologies predefined by criteria external to the TPEC will be specified implicitly by means of samples of DPs of TPEC of patients with the contained pathologies of interest in a database. The objective of the statistical analysis in this case is to determine the probability that the TPEC is obtained from a subject with the specified illnesses.

Groups determined by methods of Unsupervised Pattern Recognition the basis of the DP of the TPEC of a sample of normal and/or pathological subjects have in common physiological characteristics of interest. The objective of the statistical analysis in this case is to determine the probability that the TPEC is obtained a subject with the physiological characteristics.

Groups consisting of a sample of DP of TPEC obtained in previous moments from the subject under study. The group of DPs for each analysis moment constitutes a vector time series. The objective of the statistical analysis of this vector time series is twofold 1. To determine the changes with time in the functioning of predetermined parts of the brain or heart, as reflected in changes of the DP, with the objective, for example, to monitor the states of the brain during an operation; and
2. To carry out predictions about the probability of that a vector of DP that reflect the functional state of the brain or heart take on a given set of values at a moment posterior to the current examination.

For the calculation of the previous probabilities, it is required to have the mean $\mu_x(v)$, and variance $\sigma_x(v)$, of each test Group for each one of the parameters at each point of the lattice of the generating volume. These means and variances can be expressed as a function of control variables, v, by means of non-parametric regression (Hastie, T. J. and Tibshirani, R. J. (1990): Generalized additive models. Chapman and Hall, Pp 18–20; ISBN 0-412-34390-8 and Fan J. and Gibjels. I. Local Polynomimal Modeling and its Applications, 1996):

$$T(x) = \mu_x(v) + \epsilon_x(v), \quad (28)$$

The following transformations are carried out, also, on the DP:

1. Transformation toward a target distribution by means of a non-linear function $x=T(DP)$, to ensure that the vector x has a distribution close to one selected, f, specified beforehand.
2. Calculation of the $z_x$ transformation using the univariate variant.
3. Calculation of the probability that all or part of $z_x$ reaches a prespecified maximum or minimum value. This calculation should be carried out with the correction of the effect of the multiple spatial and temporal correlations. These are as much a consequence of the estimation process as of the physiology of the brain and heart, the over all effect being of increase the type error I in the identification of pathological states.

The complexity of this problem rests in the nature of $z_x$ as a random function defined on a four dimensional manifold, three dimensions for space and one for time (defined so without loss of generality, though the time dimension may refer to an expansion in a basis of a Megadictionary; thus also possibly defining a frequency or time frequency dimension). Statistical methods have been developed for this type of random variable defined as a stochastic processes on a n-dimensional manifold (Worsley, K. J., Marrett, S., Neelin, P., Vandal, A. C., Friston, K. J., and Evans, A. C. (1995): A unified statistical approximation for determining significant signals in images of cerebral activation. Human Brain Mapping, 4:58–73). These statistical procedures have been applied to the study of structural images (CAT, MRI), as well as functional images (fMRI, SPECT, and PET). Said methods have not been applied yet to the field qEEG/qEKG or to the TPEC. In particular these results calculate the probability P that $z_{max}$, the maximum value of z observed in a region of interest C (of arbitrary shape), exceeds a given threshold U.

$$P_{f,max}(z_{max} > U) \sum_{d=0}^{D} \rho_{max}(f)_d \cdot R_d(C)$$

$$P_{f,min}(z_{max} < U) \sum_{d=0}^{D} \rho_{min}(f)_d \cdot R_d(C)$$

where $\rho_{max}(f)_d$ y $\rho_{min}(f)_d$ depend on the type f of random field that is postulated (Gaussian, t, F, $\chi^2$, etc.) and the Rd characterizes the geometry of C being expressed in terms of the FWHM of the stochastic field. FWHM=$mt;epmrl;\sqrt{4}$ loginfbeginitaleenditalresetbeginbold2endboldrlxmx(det $(\Lambda))^{-1/2D}$, where $$\Lambda = Var\left(\frac{\partial Z}{\partial x}\right)$$

is the variance of the derivative of the stochastic field, and D is the dimension of C. Notice that, in the general case, the probability previously expressed only will depend on the type of random field that is being evaluated but also on the degrees of freedom of the statistical image.

$z_x$ will be plotted in the following ways

As one-dimensional graph, where $z_x$ will be plotted as a function for a fixed point of the lattice. This graph type is denominated a z curve (or, in the case of the frequency domain, z spectrum of the TPEC).

As a two or three-dimensional image, where $z_x$ will be plotted for a fixed time instant. This graph type is denominated z image of the TPEC. The plot will be carried out according to a color code that indicates the degree of deviation of the TPEC from normative values.

This plot is superimposed on an anatomical atlas, which constitutes the background of the image.

For the clearer statistical evaluation of the z image the following transformation is defined:

$$\begin{cases} z_w = F^{-1}(P_{f,max}(z)) & si \ z \geq U_{max} \\ z_w = 0 & si \ U_{min} < z < U_{max} \\ z_w = F^{-1}(P_{f,min}(z)) & si \ z \leq U_{min} \end{cases}$$

where the region of interest selected is the complete image, $F^{-1}$ is the inverse Gaussian distribution function. $U_{max}$, $U_{min}$ are limits chosen by the user, a possible selection being $U_{min} = -U_{max}$. The resultant is a scale of probability corresponding to a univariate gaussian distribution. The advantage of this is that the user can make an evaluation without having to keep in mind the distribution type f or the corresponding degrees of freedom.

EXAMPLES OF PREFERRED EMBODIMENTS

TPECc in the Frequency Domain

One preferred, but non-exclusive, embodiment of this invention will be the TPECc in the frequency domain for the EEG. This embodiment is developed for situations in situations in which it is not convenient to obtain an individual MRI and therefore the use of Probabilistic Brain Atlas becomes necessary. The observations are taken now as the EEG for the individual i, segment j, which is modeled (Valdés, P.; Bosch, J.; Grave de Peralta, R.; Hernandez, J. L.; Pascual, R. and Biscay, R.: Frequency domain models for the EEG. Brain Topography, 1992a, vol. 4, pp. 309–319) as:

$$o_{i,j}(t) = \kappa_i \cdot v_{i,j}(t) - \beta_{i,j}(t) \cdot 1_{N_d}, \quad (29)$$

In other words, it is assumed that the observed EEG is the distortion of an ideal recorded EEG $v_{i,j}(t)$ by multiplication with a scale factor $\kappa_i$ (individual and random) and also by subtraction of the activity of the reference electrode $\rho_{i,j}(t)$.

By means of visual inspection, it is guaranteed that the segments conform to the assumptions of stationarity and "mixing" (Brillinger, D. R, (1975): Time series Date Analysis and Theory.). This guarantees that the Fourier transformed of the segments $o_{i,j}(\omega) \sim N_C^{Nd}(0, \Sigma_o(\omega))$ where $\omega$ indicates frequency and the crosspectral or covariance matrix of the EEG which is estimated as:

$$S_{O,i}(\omega) = \frac{1}{N_{seg}} \sum_{j=1}^{N_{seg}} o_{i,j}(\omega) \cdot o_{i,j}(\omega)^*, \quad (30)$$

Valdés-Sosa (Valdés-Sosa, P. (1984): Statistical Bases. Chapter 7. Neurometric assessment of brain dysfunction in neurological patients. In: T. Harmony. Functional Neuroscience, vol. 3, Lawrence Erlbaum Associates, Hilsdale, N.J., pp. 141–254). Consequently the sample estimator of the matrix of covariances $\Sigma_i(\omega)$ is:

$$S_{V,i}(\omega) = \frac{1}{\kappa_i^2} H \cdot S_{O,i}(\omega) \cdot H, \quad (31)$$

where H denotes the centering matrix that transforms the data to the average reference (Mardia K V, Kent J T and Bibby J M. (1979): Multivariate Analysis. Academic Press Inc. London Ltd.) and the Maximum Likelihood estimator of $\kappa$ is described in Hernandez et al. (Hernández, J. L.; Valdés, P.; Biscay, R.; Virués, T.; Száva, S.; Bosch, J.; Riquenes, A. and Clark, I. (1995): A Global Scale Factor in Brain Topography. Intern. Journal of Neuroscience, 76:267–278).

In this case, the object of primary interest is the estimation of $\Sigma_{J_i}(\omega)$ which is carried out by choosing the appropriate a priori probabilities. In this case, the MAP estimation procedure is equivalent to minimize the following expression:

$$\sum_{r=1}^{N_{seg}} \left( (v_{ir}(\omega) - K \cdot j_{ir}(\omega))^t \cdot \sum_{E_i}^{-1}(\omega) \cdot (v_{ir}(\omega) - K \cdot j_{ir}(\omega)) + \right. \quad (32)$$

$$\left. j_{ir}^t \cdot \sum_{J_i}^{-1} \cdot j_{ir} \right) + (m + N_{seg}) \cdot \ln\left|\sum_{J_i}(\omega)\right| + \frac{1}{\tau_i^2(\omega)} Tr\left\{\sum_{J_i}^{-1}(\omega) \cdot G\right\}$$

which is achieved by calculating iteratively for the step k

1. $-A_{j_i}(\omega)^{(k)} =$ (33)

$$\sum_{J_i}(\omega)^{(k-1)} \cdot K^t \cdot \left(K \cdot \sum_{J_i}(\omega)^{(k-1)} \cdot K^t + \sum_{E_i}(\omega)\right)^{-1} \cdot S_i^{\frac{1}{2}}(\omega)$$

2. $-\sum_{J_i}(\omega)^{(k)} = \dfrac{N_{seg} A_{j_i}(\omega)^{(k)} \cdot A_{j_i}(\omega)^{(k)} + \dfrac{1}{\tau_i^2(\omega)^2} G}{m + N_{seg}}$ These steps are repeated until the estimator converges.

In equation (32) the first term corresponds to the likelihood, the second term $$\sum_{r=1}^{N_{seg}} j_{ir}(\omega)^t \cdot \sum_{J_i}^{-1}(\omega) \cdot j_{ir}(\omega),$$

to the usual regularizing term with the hyperparameter matrix. The third term corresponds to the natural conjugate a priori for the Wishart Matrix for the hyperparameter $\Sigma_{J_i}(\omega)$, proportional to:

$$G = (\Lambda_m \cdot L^t \cdot \Lambda_s^2 \cdot L \cdot \Lambda_m)^{-1} \otimes I_3$$

where the diagonal matrix $\Lambda_s$ specifies the degree of smoothness that will be enforced in each point of the lattice (in this case, 0 for the borders of the gray matter). $\Lambda_m$ weights the permissible magnitude of the PEC at each point of the lattice $$\Lambda_m = W \cdot \Lambda_G^{\frac{1}{2}},$$

where the diagonal matrix $\Lambda_G$ contains an estimator of the probability that any normal brain has gray matter at that position. These probabilities for example can be obtained using a Brainl Probabilistic Atlas (Evans, A. C., Collins, D. L., Neelin, P., MacDonald, D., Kambei, M., and Marret, T. S. (1994) Three dimensional correlative imaging: Applications in human brain mapping. In R. Thatcher, M. Hallet, T. Zeffiro, E. Roy John and M. Vegetable garden (Eds.) Functional neuroimaging technological foundations. Academic Press; Mazziotta J C, Gown T O, Evans A C, Fox P, Lancaster J (1995) A probabilistic atlas of the human brain: Theory and rationale for its development. Neuroimage 2: 89–101).

In a particular embodiment of this invention, the diagonals of all $\hat{\Sigma}_{j_i}(\omega)$ are taken as DP, denoted as $S_j(\omega)$. Equation (28) is applied to each one of these descriptive parameters using the natural logarithm as T. The mean and variance by frequency and for each point of the lattice are obtained previously by the regression model:

$$\ln(S_{j,i}(\omega)) = \mu_i(\omega;\text{age}) + \epsilon_i(\omega;\text{age}) \quad (34)$$

where the population the mean $\mu_i(\omega;\text{edad})$ and standard deviation $\sigma_i(\omega;\text{age})$, for each point of the lattice j and each age, are obtained by heteroscedastic non-parametric regression (Hastie, T. J. and Tibshirani, R. J. (1990): Generalized additive models. Chapman and Hall, Pp 18–20; ISBN 0-412-34390-8; Fan J. and Gibjels. I. Local Polynomimal Modeling and its Applications. Chapman and Hall). The complete set of $\mu_i(\omega;\text{edad})$ constitutes then a generalization of the developmental surfaces described in Valdés et al. (Valdés, P.; Biscay, R.; Galán, L.; Bosch, J.; Szava, S.; and Virues, T.: High Resolution Spectral EEG norms for topography. Brain Topography, 1990, vol. 3, pp. 281–282) and now extended to the TPEC. In FIG. 9, these regression surfaces (obtained from the Cuban Normative EEG Data Base) can be observed. In the figure, three-dimensional surfaces are shown for several points of the generator lattice, in which the z-axis is $\mu_i(\omega;\text{edad})$ the y-axis is frequency and the x-axis is age.

The two or three dimensional plots of the z values obtained this way from $S_j(\omega)$ constitute an example of z images of the TPEC. The plotting is carried out with a color code that indicates the deviation of the calculated image from normative values. This plot is superimposed on a cerebral atlas in Talairach coordinates, which constitutes the background of the image. For the statistical evaluation of z images of it is assumed that they are samples of a four dimensional gaussian random field (3 space and 1 frequency dimensions). In this case the theory described by Worsley et al. is applied (Worsley, K. J., Marrett, S., Neelin, P., Vandal, A. C., Friston, K. J., and Evans, A. C. (1995): A unified statistical approximation for determining significant signals in images of cerebral activation. Human Brain Mapping, 4:58–73). This allows the evaluation of the probability that a maximum or minimum of the image z takes a given value. The $z_w$ transformation described above is adopted for the yielding a scale of probability corresponding to a univariate gaussian distribution.

Clinical Example 1

In FIG. 10, a) the Z image of the TPECc in the frequency domain is shown, said image being obtained from a 27-year-old female patient for whom an astrocytoma in the left fronto-parietal region had been diagnosed. For purposes of comparison also shown in this figure are the b) spiral CAT, c) T1 MRI, d) SPECT, and and e) T2 MRI.

Clinical Example 2

A group of 11 neurological patients of recent admission were selected based on a diagnosis of Cerebrovascular accidents (CVA) of ischemic origin, due to occlusion of the Left (LCMA) or Right (RCMA) Medial Cerebral Artery. TCEPc the frequency domain and the CAT were applied to all patients. Examples of the obtained TPECc-FD are shown in FIG. 11, there being a complete correspondence with the clinical diagnosis. In Table1, all the results obtained are summarized. One can observe that in 7 cases the TPECc-DF was superior to the CAT, in 3 equal and only in 1 worse in terms of localization accuracy. The CAT is to date the imaging method of election for evaluation of CVA in spite of its invasive nature.

TABLE 1

| PATIENT | AGE IN YEARS | MOMENT OF THE STUDY IN HOURS | I DIAGNOSE | TPECc-DF | CAT |
|---|---|---|---|---|---|
| 01-FIG. 11a | 48 | 12 | LCMA | YES | NO |
| 02I | 75 | 24. | LCMA | YES | NO |
| 03 | 44 | 48 | LCMA | YES | NO |
| 04 | 71 | 24 | LCMA | YES | NO |
| 05 | 49 | 48 | LCMA | YES | NO |
| 06 | 65 | 22 | RCMA | YES | NO |
| 07-FIG. 11b | 72 | 16 | RCMA | YES | NO |
| 08 r | 62 | 24 | RCMA | YES | YES |
| 09 | 69 | 48 | LCMA | YES | YES |
| 10 | 48 | 48. | LCMA | YES | YES |
| 11* | 66 | 24 | LCMA | NO | YES |

Non-Linear Analysis of $\gamma(x,t)$

Another preferred, but not exclusive, embodiment of this invention is the TPECc in the time domain. In this case, the method is used to identify activated cerebral regions and their functional connections when one has an individual anatomical brain atlas for the subject under study. The values $\gamma(x,t)$ are defined by the quantities $\gamma_m(t)=f_m(t)$, $m=1, 2, 3, 4, 5$ and $\gamma_6(t)=a(t)$ which is fitted using a Nonparametric Nonlinear Autoregressive Model (NNAM): $\gamma_t=F(\Gamma_t^q,t)+\epsilon(\Gamma_t^q,t)$, where $\Gamma_t^q=[\gamma_{t-k}]_{1 \leq k \leq q}$ is the matrix of pasts which constitutes the previous state of the Markovian system (q is the maximal order of the past included). Both the Autoregressive function F as well as the matrix of covariances, $\Sigma_\gamma(\Gamma_t^q,t)$ of $\epsilon(\Gamma_t^q,t)$ are dependent, both on the previous state as well as on the time instant t, for which reason the model is also non-stationary and heteroscedastic. Both the Autoregressive function F as well as the matrix of covariances, $\Sigma_\gamma(\Gamma_t^q,t)$ are estimated using non-parametric methods (Hastie and Tibshirani, 1990) in the form of Splines (Wahba, 1990), local polynomials (Fan J. and Gibjels. I., Local Polynomimal Modeling and its Applications. Chapman and Hall), SVM (Smola A., (1996) Regression Estimation with Support Vector Machines. Ph.D. Dissertation Physik Department, Technische Department, Technische Universität München) or regression in Megadictionaries.

The evaluation of F on the support of the series of time $\gamma_t$ generates a vector $x_\gamma^{NL}$ of DP that contains information about the morphology of the grapho-elements of the physiological series, which has been demonstrated to be more informative than the one provided by polyespectra for the recognition of the activity of ictal activity in the EEG of epileptics (Hernández, J, L., Valdés, P. A., and Vila, P. (1996) EEG spike and wave modeled by to stochastic limit cycle. NeuroReport, 7: 2246–2250). The cluster analysis and pattern recognition of the EEG is carried out now with $x_\gamma^{NL}$, using for this purpose not only simple linear methods but also non Parametric methods (Ripley B. D. (1966) Pattern Recognition and Neural Networks. Cambridge University Press).

Additionally, the estimate of F allows the calculation of estimates of Granger causality among generators of PEC by means of the following non-linear and non-stationary generalization of influence measures introduced by Geweke (1984). Let us denote for A, B and C as subsets (with an empty intersection) of the time series of that comprise $\gamma_t$. Let us define the matrix of covariances $\Sigma_\gamma(\Gamma_t^q, t; A|B.C)$ as the one obtained from A when the influence of B is eliminated by non parametric regression conditional on C. Then the (directed) influence of B on A, conditional to C as the natural logarithm of the ratios of determinants:

$$I_{B \to A/C} = \ln \left( \frac{\left| \sum_\gamma (\Gamma_t^q, t; A | \{\}.C) \right|}{\left| \sum_\gamma (\Gamma_t^q, t; A | B.C) \right|} \right)$$

The potential utility of the influence measures combined with the TPECc in the evaluation of the epileptic pathology is now illustrated. Estimators of $\gamma_t$ were obtained based on the EEG recording of a patient with a complex partial seizure (of focal origin and secondary propagation resulting in loss of consciousness). The patient was an 11 year-old girl whose recording is shown in FIG. 12. In FIG. 13, the estimated variance of $\gamma_t$ is shown it being possible to observe four active sites (indicated with the letters A to D in the figure). The calculation of the influence measures indicated the direction of flow of the information among presumed epileptic foci. As can be seen focus A influenced all the other presumed foci and others did not influence it. The place of greatest activity and presumed primary origin of the crisis was considered as A, which corresponded to the clinical diagnosis.

Figure 1:
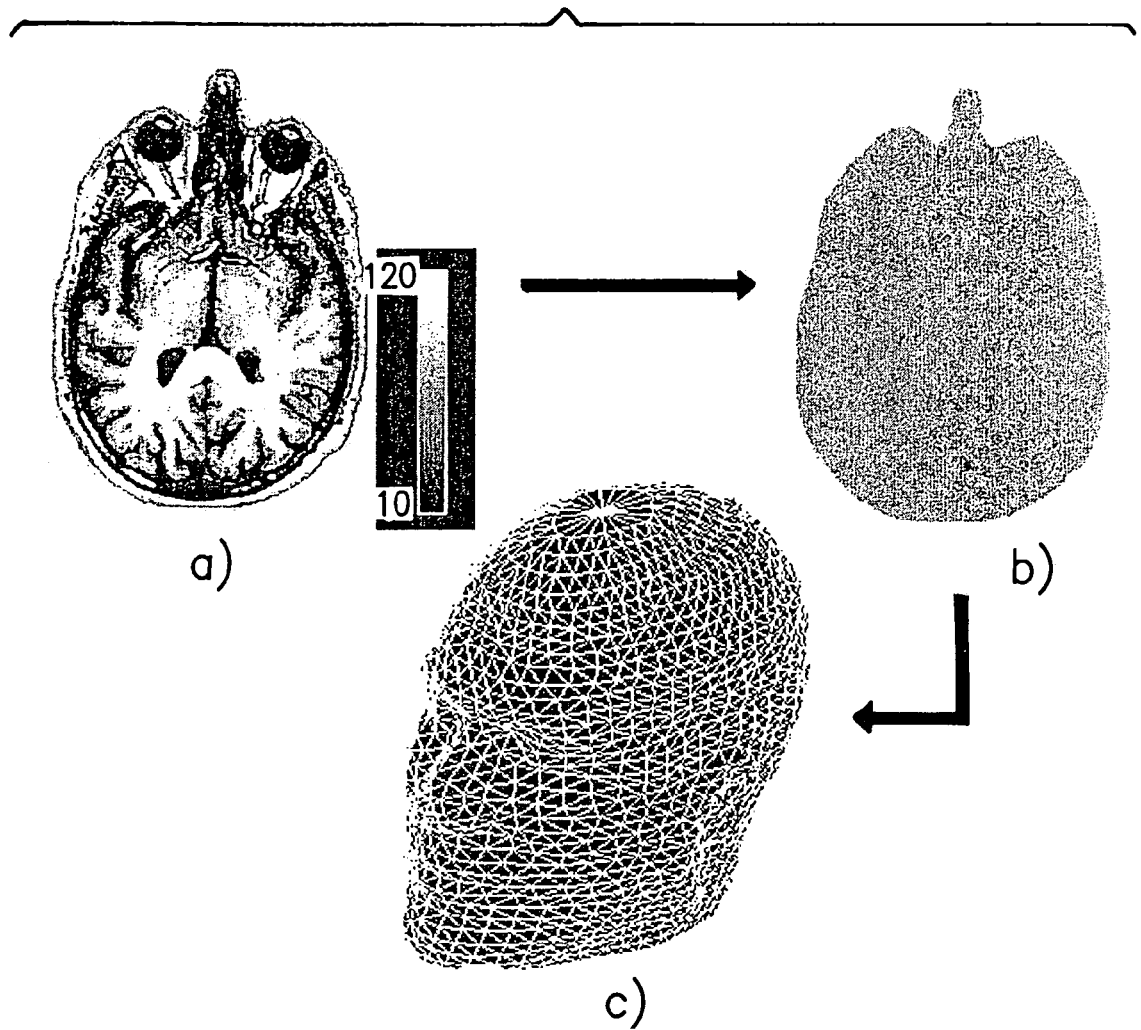
FIG. 1
Figure 2:
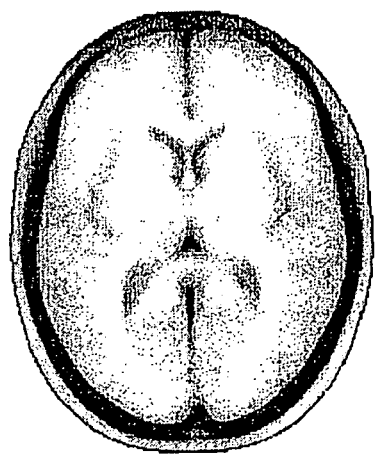
Figure 2:
Figure 2:
Figure 2:
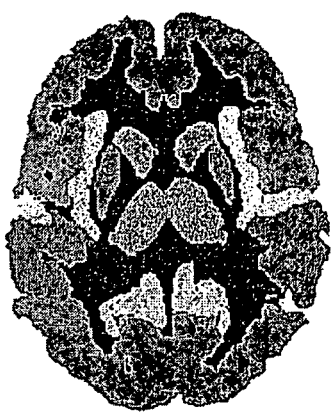
Figure 3:
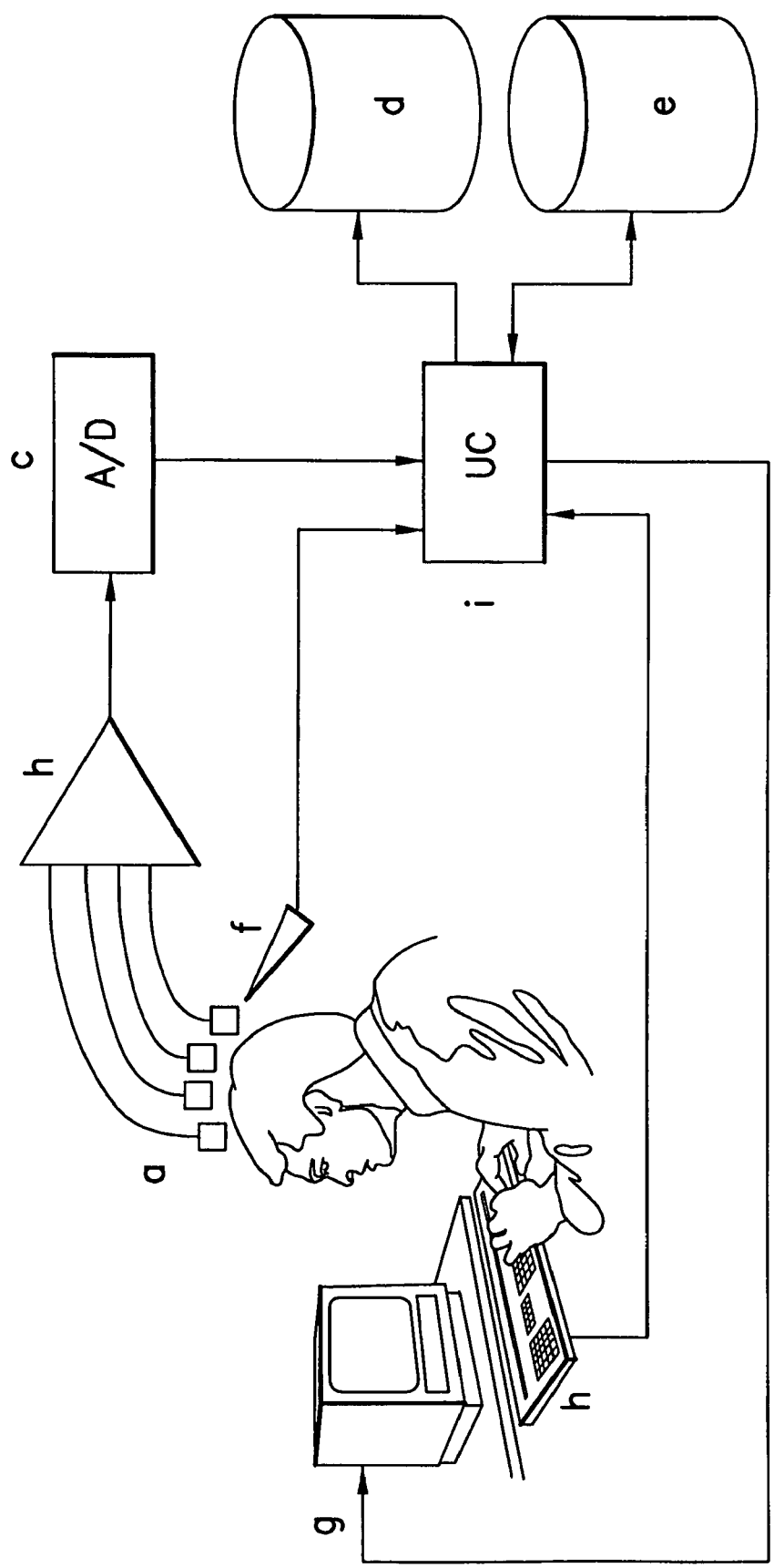
Figure 4:
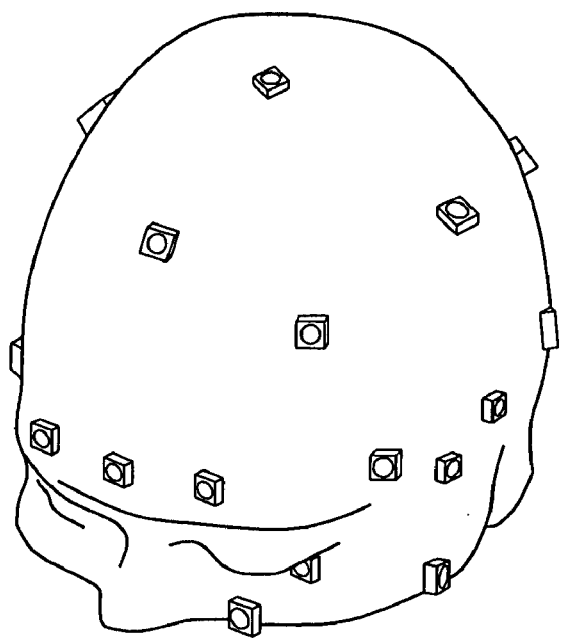
Figure 5:
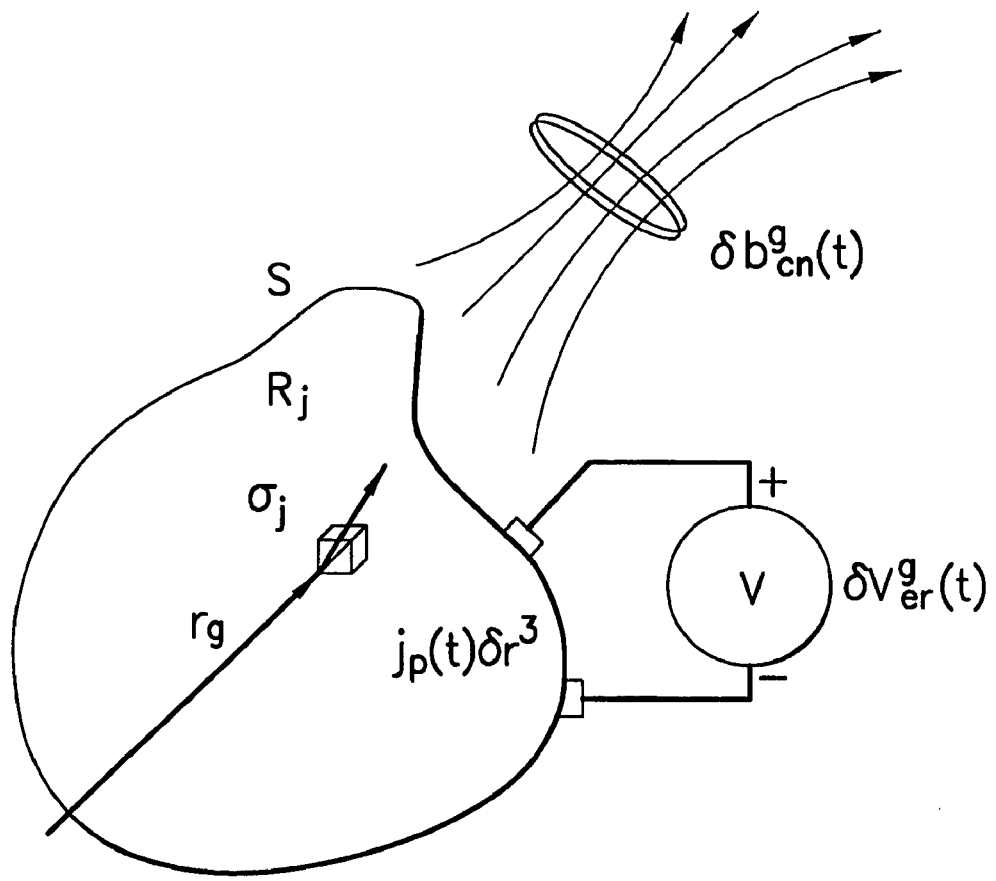
Figure 6:
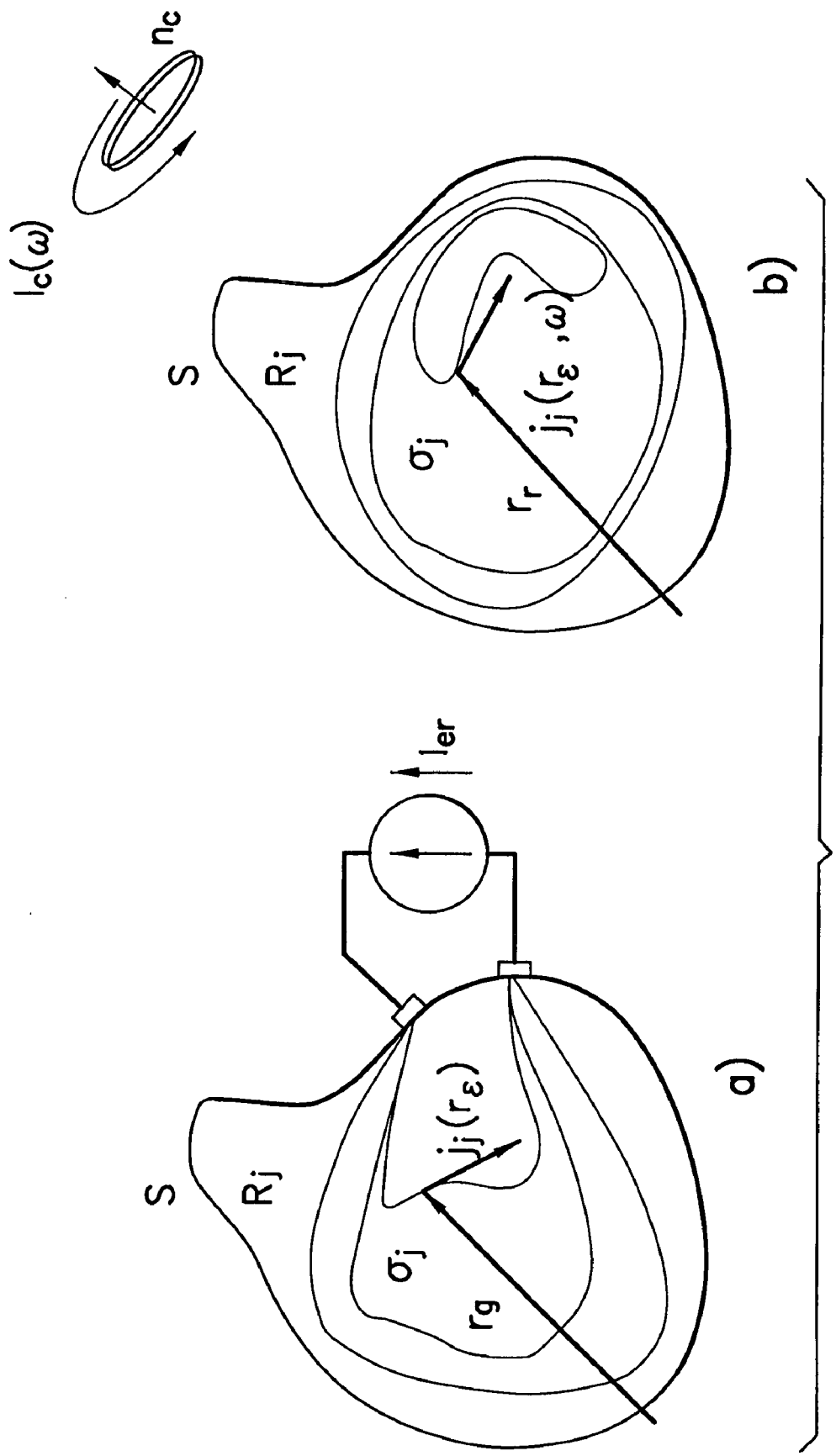
Figure 7:
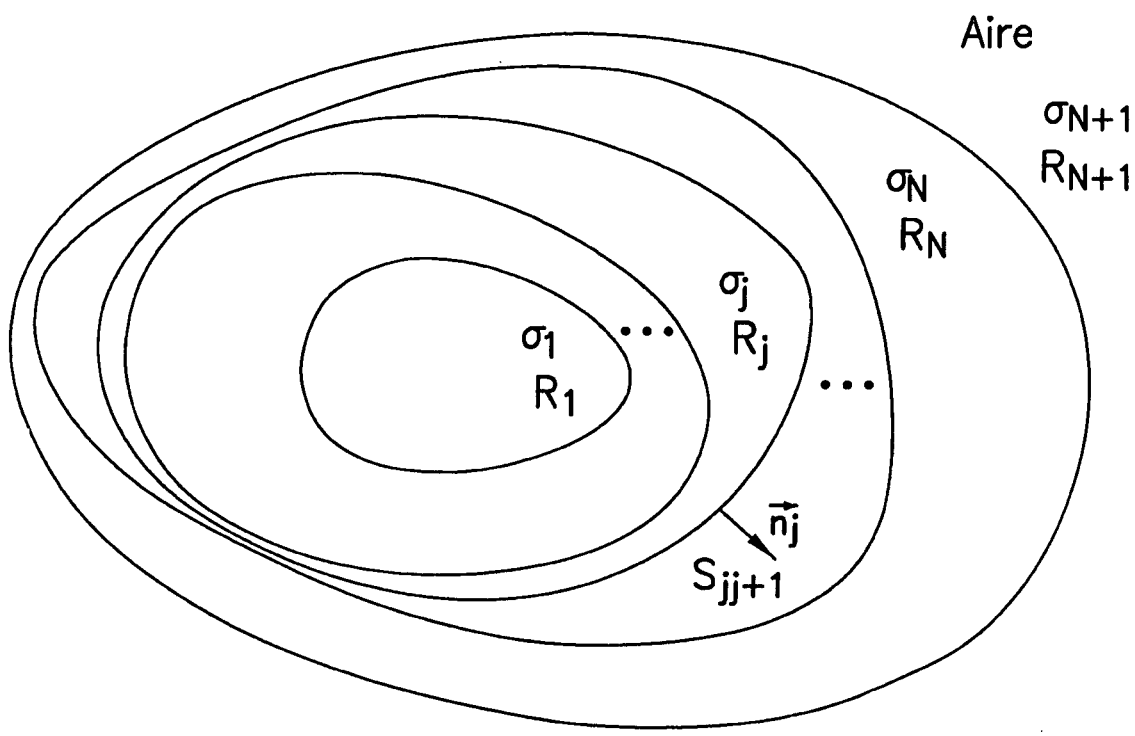
Figure 8:
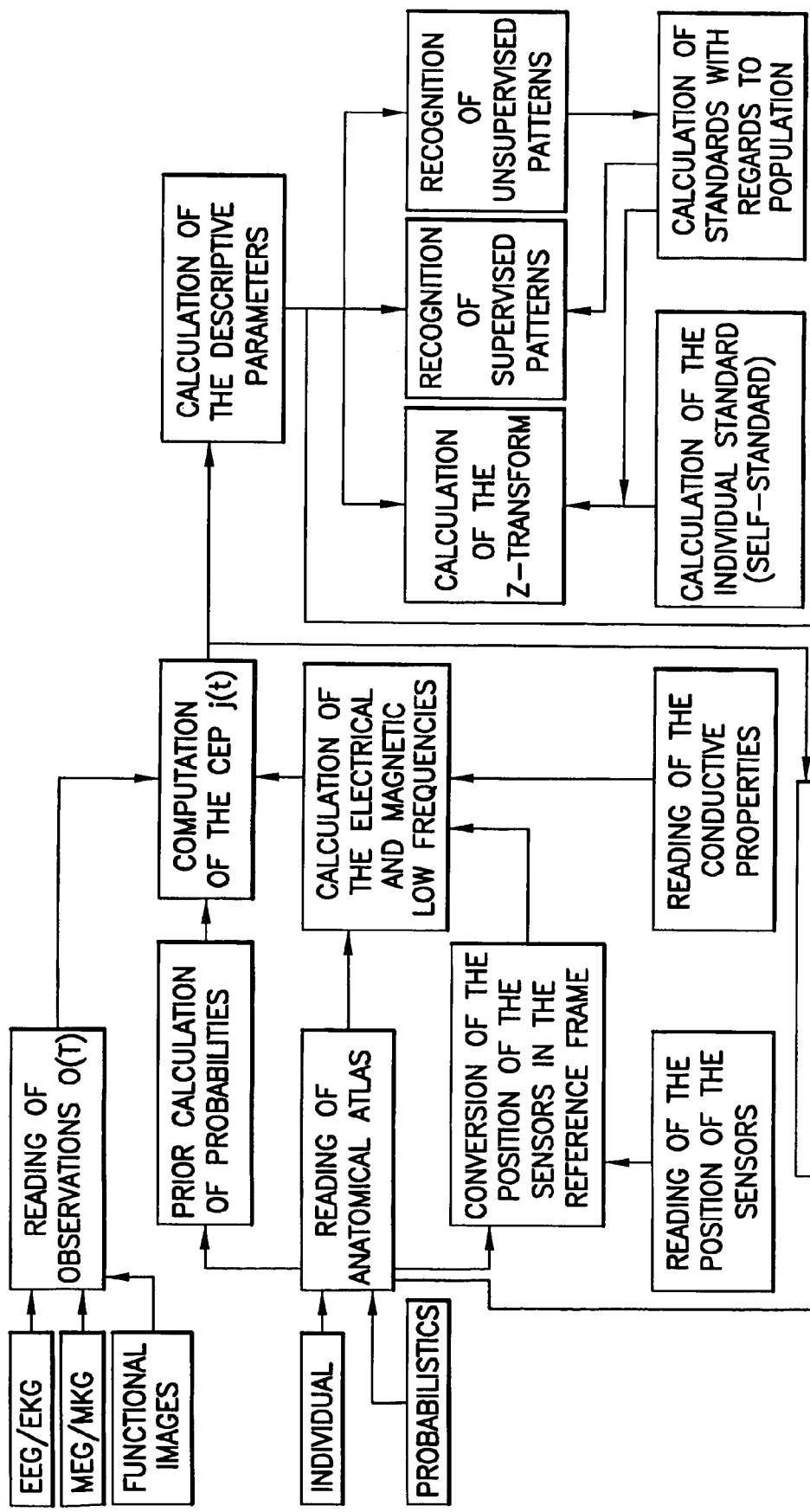
Figure 9:
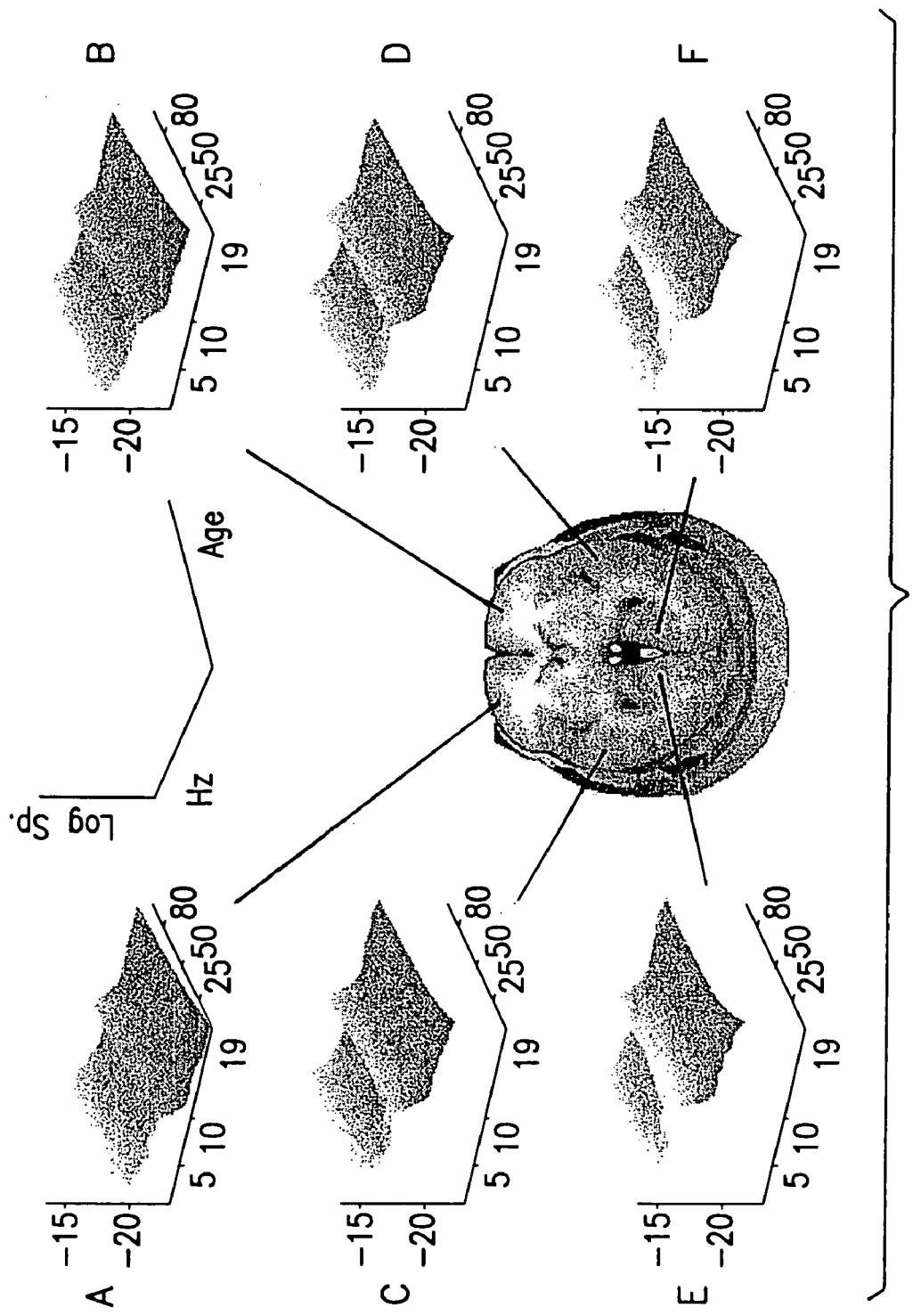
Figure 10:
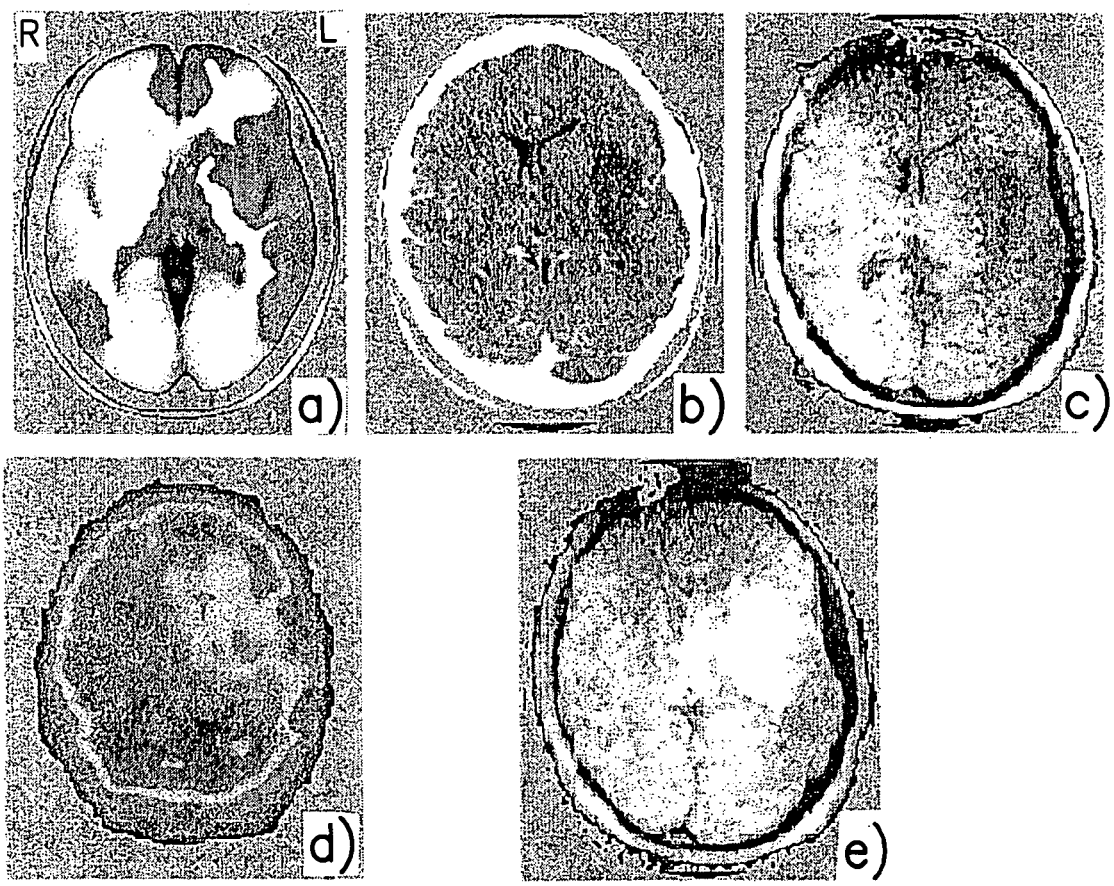
Figure 11:
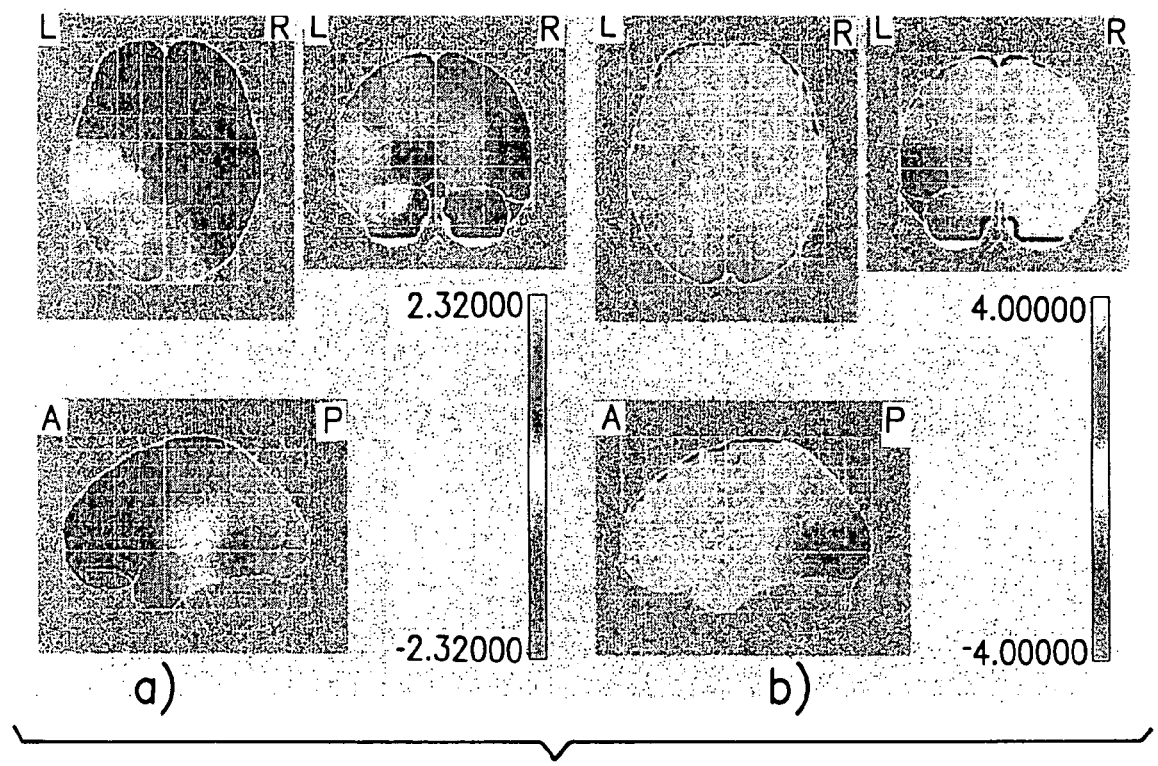

Cerebral anatomical atlas based on an individual structural image. a) Axial slice of a MRI, to which a procedure of contour detection is applied; b) Outline of the detected skin; c) 3D reconstruction of the triangulation of the surface of the skin using the contours detected in all the slices.

FIG. 2

Cerebral anatomical atlas based on a probabilistic structural image in the Talairach reference system. a) Axial slices of the average image; b) image of the probability of appearance of gray matter; c) image of the probability of appearance of the gray matter of the occipital lobe; d) segmentation of different structures of the gray matter represented by a discrete scale of colors.

FIG. 3

This figure is a diagram showing a System for obtaining the TPEC, comprising the following parts presented here, without loss of generality, for the particular embodiment for the TPECc. These elements are those described next and designated by the letters used for their identification: a) A plurality of external sensors of electric and/or magnetic fields which are placed in the proximity of the subject's body. In the case of TPECc, said sensors are placed in the proximity of the subject's head. In the case of TPECk, said sensors are placed in the proximity of the subject's torso. These sensors are connected to the amplification sub-system (b) consisting of electronic pre-amplifiers and amplifiers that record the signals picked up by said sensors and that carry out the pre-conditioning of these signals for their later analog to digital conversion. The amplification sub-system is connected to the sub-system of analog to digital conversion (1–c) that transforms the amplified signals into a sequence of binary numbers. Said analog to digital conversion sub-system is connected to a general-purpose digital computer that acts as a control unit (CU). (i) The digitized signals are stored in the memory of the CU, which is, in turn, coupled to external sub-systems for digital storage (d) and that allow the reading and storage of:

Anatomical atlas of the brain or of the heart in the reference system of the head or the torso, respectively.

Functional images of the brain or heart of a subject obtained by other biophysical procedures and defined in the reference system of the head or of the torso.

The system also comprises a device for detecting the position of sensors (f) that emits in digital form, the coordinates of these sensors as well as the coordinates of external anatomical structures of the subject's head or torso. These coordinates are defined in said reference system, and are stored in the CU. Additionally, the system comprises a plurality of stimulating devices (g) connected with the CU that emit auditory, visual sensorial stimuli, as well as heat, electric, and magnetic pulses for the purpose of stimulating the subject's nervous or cardiovascular system. To the CU are also connected a plurality of sensor devices (h) that measure the motor, physiological and verbal reactions of the subject under study (Responses of the subject). The CU (i) is a general-purpose computer in whose memory a group of instructions resides (Programs) for the control of the realization of studies. The activities of the system for TPEC that are controlled by this program include: the activation of the stimulating devices according to a preset design (conceived with the purpose of exploring reactions of the subject); the control of the acquisition of the EEG/MEG/EKG/MKG; the determination of the positions of the sensors; the recording of the activity of the subject under study in the same time reference system as that of the EEG/MEG/EKG/MKG; the acquisition of the functional images coming from other biophysical modalities; and the digital processing of all the information acquired in a study of a subject for the construction of three-dimensional statistical maps of the temporal evolution of the functional states of the brain.

FIG. 4

Electrodes of the standard 10/20 system for the recording of the EEG shown on the skin of the probabilistic brain atlas in Talairach reference system.

FIG. 5

Illustration of the principle of reciprocity for a compartment $R_j$ surrounded by a surface S of arbitrary shape. Elemental voltage difference $\delta V_{er}^g(t)$ and projection of the magnetic vector field $\delta b_{cn}^g(t)$ that appears due to the presence of a point PEC $j_P(t)\delta r^3$ inside the compartment $R_j$.

FIG. 6

Illustration of the principle of reciprocity for a compartment surrounded by a surface S of arbitrary shape. Densities of ohmic currents that appear inside the $R_j$ compartment in the absence of active PEC, as a result of energizng the: a) electric sensors with a direct current $I_{er}$ and b) the magnetic sensors with an alternating current $I_c(\omega)$ of low frequency.

FIG. 7

Graphical representation of an isotropic piecewise homogeneous volume conductor (IPHC).

FIG. 8

Sequence of operations with the subject. The use of the system described for obtaining TPEC consists of the following operations: Placement of the subject in seated or lying position in the proximity of the system described. Positioning of a group of sensors (electrodes and magnetic sensors) in order to detect and to record the electric and magnetic signals that represent the cerebral and heart physiological activity in the form of recordings of EEG/MEG/EKG/MKG. Use of the device for the measurement of the coordinates of the sensors and the external anatomical structures of the head or the torso for their storage in the memory of the CU. Initiation of the collection of data of the subject, controlled by the programs stored in the memory of the CU. Gathering and analog to digital conversion of the electric and/or magnetic activity of the brain or heart of the subject by the use of the systems for amplification and analog to digital conversion. This step may optionally be accompanied by the presentation of stimuli using the devices described and the acquisition of the Responses of the subject. The picked up signals are stored in form of chronological series of EEG/MEG/EKG/MKG. Removal of the subject from the system. Pre-processing of the signals recorded from the subject for the elimination of artifacts and of non-physiological frequency components.

Sequence of operations used by the Program.

Input of the observations (EEG/EKG; MEG/MKG; optionally of functional Images such as fMRI, PET, SPECT).

Input of the positions of the sensors.

Input of an anatomical atlas, this may be either an individual or a probabilistic structural image.

Conversion of the position of the sensors to the reference system of the anatomical atlas.

Calculation of the a priori probabilities obtained from the anatomical atlas.

Input of the conductive properties.

Calculation of the electric and magnetic LFs using the positions of the modified sensors.

Calculation of the PEC j(t).

Calculation of observable descriptive parameters (DP) of the preprocessed signals already. These DP are sufficient statistics of models of stochastic processes. Particular, but not exhaustive, instances of these statistics are:

Averages, variances and covariances or higher order cumulants calculated as invariant in the time or, alternatively, as non-stationary.

cross polyspectra of all the channels of recorded EEG/EKG and MEG/MKG, calculated as invariant in the time or, alternatively, as non-stationary;

Multivariate Autoregressive functions fitted to the EEG/EKG and MEG/MKG, both parametric (linear, quadratic) as well as non-parametric.

Correlation measures, mutual information, Granger causality between channels of EEG/EKG and MEG/MKG.

Regression coefficients of any one of the previous types of parameters with respect either to the stimuli emitted by the system or to the subject's answers.

FIG. 9

Illustrates the equations that describe the normal variation of the TPECc in the frequency domain. Each sub plot shows, for points of the representative cerebral lattice, the regression surface of the logarithm of the spectrum of the PEC (axis z) with regard to frequency (x) and age (z).

FIG. 10

Z image of the TPECc in the frequency domain of a 27 year old female patient who was diagnosed as having an astrocytoma in the left fronto-parietal region of the brain. For purposes of comparison other imaging modalities for this patient are shown in b) spiral CAT, c) T1 MRI, d) SPECT and) T2 MRI.

FIG. 11

Maximum Intensity Projection of the Z transform of the logarithm of the TPECc in the frequency domain of two patients with Cerebrovascular Accident of the a) Left and b) Right Middle Cerebral Artery.

FIG. 12

EEG recording of a patient with complex partial epilepsy. The recording presents spike and wave activity.

FIG. 13

Figure 12:
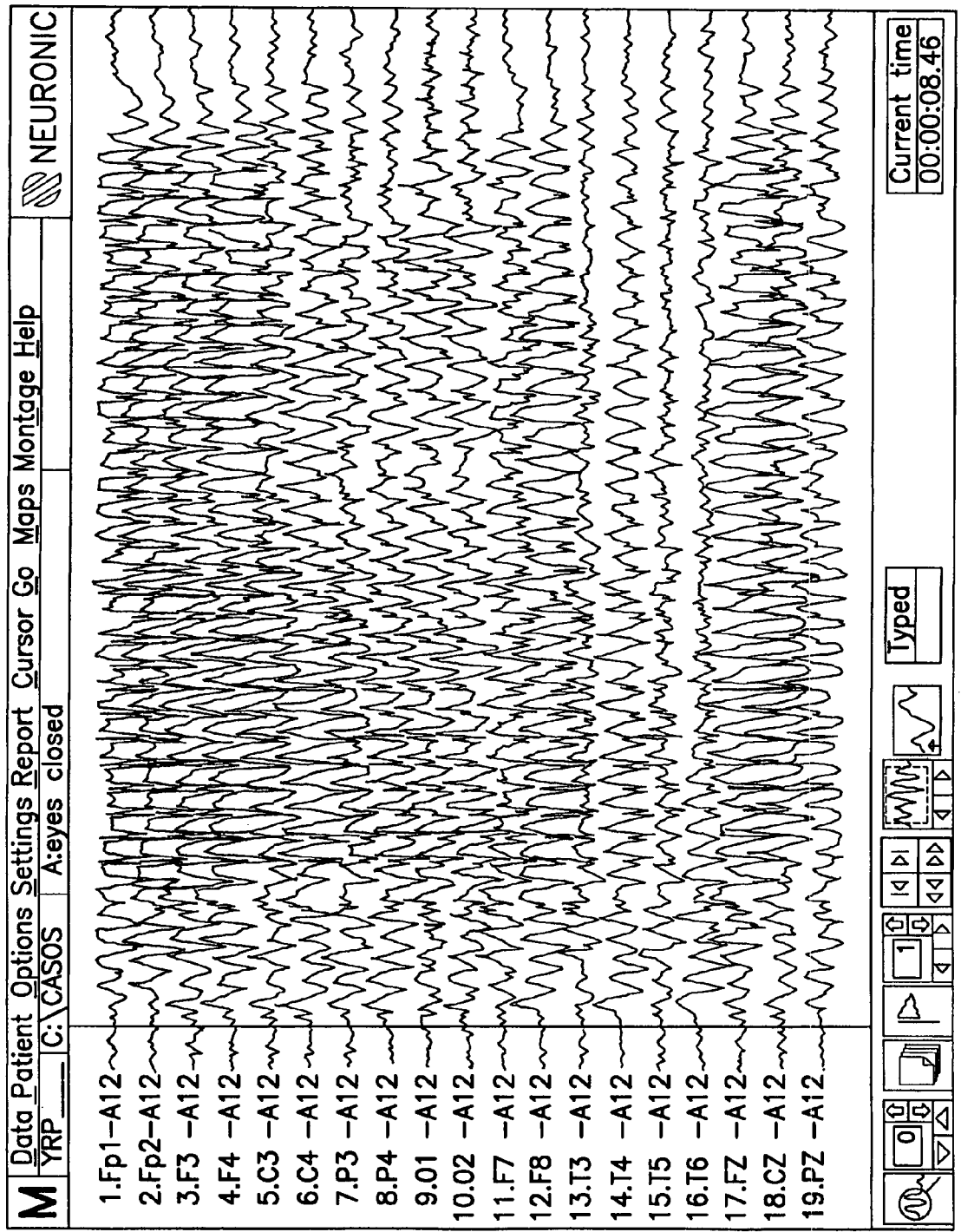
Figure 13:
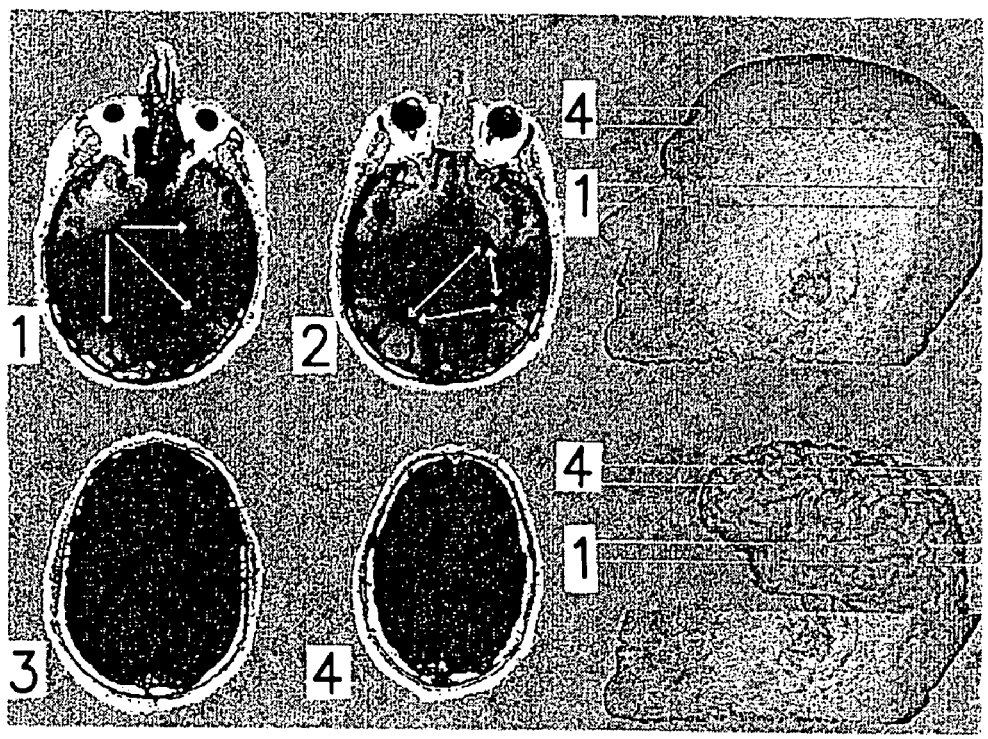

TPECc in the time domain of the recording of FIG. 12 in which the major sources of PEC are indicated as well as the direction of flow of information as determined by the measures of non-linear influence, not stationary.

We claim:

1. Method for the Tomography of the Primary Electric Current (TPEC) of the brain (TPECc) and of the heart (TPECk) comprising the following steps:

pre-processing of a plurality of signals recorded from a subject for the elimination of artifacts and of non-physiological frequency components;

conversion of a plurality of coordinates of sensors to a reference system of a respective head or torso by means of the application of a visco-elastic deformation, that puts into correspondence the coordinates of a plurality of external anatomical markers of the subject with those of a structural image stored in a computing unit (CU);

calculation of respective electric Kernel and magnetic Kernel linear operators that predict the o(t) that would be produced in the subject by the presence of the PEC j(t) in any part of the brain or heart;

calculation of the TPEC by means of Bayesian Hierarchical Estimation Procedure that determines the primary electric current j(t) of the brain or heart using structural information obtained from an anatomical atlas, metabolic information obtained from functional images, and an assumption that the solution belongs to a space of Besov space of given smoothness or determined by a norm in a Megadictionary;

calculation of descriptive parameters either on the basis of the observations o(t) directly, or of the j(t);

calculation of a probability that all or some of the DP are similar to those of a given test group; and performing the step wherein the obtained TPECc is coded by means of a pseudocolor scale and is overlaid on the anatomical atlas, a scale being fitted according to the probability previously calculated, whereby only statistically significant anatomical sites are highlighted.

2. The method of claim 1, wherein vectors of descriptive parameters (DP) are calculated that are statistics of models of stochastic processes for o(t) or j(t), wherein instances, of DP include at least one of:
- subsets of o(t) or j(t);
- subsets of o(t) or J(t) or $\mu(t)$, or $\gamma(t)$;
- subsets of averages, variances and covariances or higher order o(t) or J(t) or $\mu(t)$, or $\gamma(t)$ or of their representation in the basis of a Megadictionary;
- subsets of cross polyspectra of o(t) or J(t) or $\mu(t)$, or $\gamma(t)$ of their representation in the basis of a Megadictionary;
- subsets of parametric multivariate Autoregressive functions fitted to o(t) or J(t) or $\mu(t)$, or $\gamma(t)$ or their representation in the basis of a Megadictionary;
- subsets of non parametric multivariate Autoregressive functions fitted to o(t) or J(t) or $\mu(t)$, or $\gamma(t)$ of their representation in the basis of a Megadictionary;
- correction measures, mutual information, Granger causality among components of o(t) or J(t) or $\mu(t)$, or $\gamma(t)$ of their representation in the basis of a Megadictionary; and
- regression coefficients of any one of the previously described types of DP with stimuli emitted by the system or with the subject's responses.

3. The method of claim 1, wherein the probability is calculated that all or part of the TPEC belongs to a test group by means of at least one of a theoretical correction and means of statistical resampling methods that compensate for the effect of multiple spatial and temporal correlations, that are due both to the large number of measurements, as well as a consequence of either the estimation process or the physiology of the brain or heart, the effect of said correlations being to increase a type error I in the identification of brain or heart states, eliminating additionally the effects of the dependence of the estimated maps with experimental covariables of interest.

4. The method of claim 1, wherein test groups are constituted to evaluate at least of of an intra and an inter-individual change of brain or heart function, examples of test groups including at least one of:
- groups of subjects defined as normal by criteria external to their TPEC, which will be specified implicitly by means of a sample of DP of TPEC of normal subjects contained in a database the objective of statistical analysis being to determine the probability that the DP of the obtained TPEC is obtained from a healthy subject;
- groups of subjects defined as having pathologies predefined by criteria external to the TPEC, which will be specified implicitly by means of samples of DP of TPEC of patient with the pathologies of interest defined in a database, the objective of statistical analysis being to determine the probability that the TPEC is obtained from a subject with the specified pathology;
- groups determined by methods of Unsupervised Pattern Recognition on the basis of the DP of the TPEC of a sample having in common physiological characteristics of interest, the objective of statistical analysis is to determine the probability that the TPEC is obtained from a subject with said physiological characteristics; and
- groups consisting of a sample of DP of TPEC obtained in previous moments from the subject under study, where all of the DPs for each analysis moment constitutes a vector time series and the objective of the statistical analysis of this vector time series has two purpose: to determine changes with time in the functioning of predetermined parts of the brain or heart as reflected in changes of the DP, as well as to carry out predictions about the probability that a vector of DP will attain certain values (reflecting the functional state of the brain or heart) in a moment posterior to the current examination.

5. The method of claim 1, wherein the following statistical operations are carried out:
- Calculation of a mean $\mu_x(v)$, and variance, $\sigma_x(v)$, of each Test Group for each one of the parameters and each point of a lattice of the generating volume, said means and variances are be expressed by means of a non parametric regression as a function of control variables;
- Transformation towards gaussianity x=T(DP), using a non-linear function to obtain a vector x;
- Calculation of the z transform $z(x_t)=(x_t-\mu_x(v))/\sigma_x(v)$;
- Calculation of the probabilities that $z_{max}$ and $z_{min}$, the maximum and minimum value of z in a region of interest C respectively, exceeds a threshold U;
- Calculation of the following transformation:

$$\begin{cases} z_w = F^{-1}(P_{f,max}(z)) & si\ z \geq U_{max} \\ z_w = 0 & si\ U_{min} < z < U_{max} \\ z_w = F^{-1}(P_{f,min}(z)) & si\ z \leq U_{min} \end{cases}$$

in which the complete image is adopted as the region of interest, $F^{-1}$ is an inverse gaussian function $U_{max}$, $U_{min}$ are thresholds chosen by the user;
- $z_x$ or $z_w$ are plotted as a one-dimensional graph where the point of the lattice is fixed, said graph being denominated a z curve or, in the case of the frequency domain, z spectrum of the TPEC; and
- $z_x$ or $z_w$ are plotted as two or three-dimensional image where t is fixed, said image being denominated z image of the TPEC the image being rendered according to a color code that indicates the degree of deviation of the values from the normative, said image being superimposed an anatomical atlas, which constitutes the background of the image.

6. The method defined in claim 5, wherein the calculation of an element $I_{B \to A/C}$ that quantifies the directed influence of brain or heart region B on region A that is not due to the activity coming from region C comprises the steps of:
a) defining regions A, B, C as sets of arbitrary voxels $r_i \in \mathfrak{R}_g$ chosen from the generating volume
b) defining the vector valued time series: a(t) as the values of $\gamma_m(t)$ for all voxels belonging to the set A; b(t) as the values of $\gamma_m(t)$ for all voxels belonging to the set B; and c(t) as the values of $\gamma_m(t)$ for all voxels belonging to the set C
c) defining the matrices:
$A_t=[a(t),a(t-1), \ldots, a(t-k), \ldots, a(t-p)]$
$B_t=[b(t),b(t-1), \ldots, b(t-k), \ldots, b(t-p)]$
$C_t=[c(t),c(t-1), \ldots, c(t-k), \ldots, c(t-p)]$
d) defining the matrices:

$$\Gamma_t(A_t/\{\} \cdot C_t) = \begin{bmatrix} A_t \\ C_t \end{bmatrix} \text{ and } \Gamma_t(A_t/B_t \cdot C_t) = \begin{bmatrix} A_t \\ B_t \\ C_t \end{bmatrix},$$

e) calculating $$\sum \gamma(\Gamma_t(A_t \mid \{\} \cdot C_t)) = \frac{1}{N_t} \sum_{t=1}^{N_t} \varepsilon_t(\Gamma_t(A_t \mid \{\} \cdot C_t)) \circ \varepsilon_t(\Gamma_t(A_t \mid \{\} \cdot C_t)),$$

where $$\varepsilon_t(\Gamma_t(A_t \mid \{\} \cdot C_t)) = a(t) - \sum_{k=1}^{p} \alpha_k a(t-k) - \sum_{k=1}^{s} \chi_k c(t-k);$$

$\alpha_k$ and $\chi_k$, for any A and C, are estimated by minimizing:

$$E_{A|\{\}\cdot C} =$$

$$\sum_{t=1}^{N_t} (\varepsilon_t(\Gamma(A \mid \{\} \cdot C)) \circ \varepsilon_t(\Gamma(A \mid \{\} \cdot C))) K_h(\|\Gamma(A \mid \{\} \cdot C) - (\Gamma_t(A_t \mid \{\} \cdot C_t))\|);$$

$$K_h(x) = \exp\left(-\frac{1}{2}\left\|\frac{x}{h}\right\|^2\right);$$

p, s, and h being selected by cross-validation;

f) calculating $$\sum \gamma(\Gamma_t(A_t \mid B_t \cdot C_t)) = \frac{1}{N_t} \sum_{t=1}^{N_t} \varepsilon_t(\Gamma_t(A_t \mid B_t \cdot C_t)) \circ \varepsilon_t(\Gamma_t(A_t \mid B_t \cdot C_t)),$$

where $$\varepsilon_t(\Gamma_t(A_t \mid B_t \cdot C_t)) = a(t) - \sum_{k=1}^{p} \alpha_k a(t-k) - \sum_{k=1}^{q} \beta_k b(t-k) - \sum_{k=1}^{s} \chi_k c(t-k);$$

$\alpha_k$, $\beta_k$, and $\chi_k$, for any A, B, and C, are estimated by minimizing:

$$E_{A|B\cdot C} =$$

$$\sum_{t=1}^{N_t} (\varepsilon_t(\Gamma(A \mid B \cdot C)) \circ \varepsilon_t(\Gamma(A \mid B \cdot C))) K_h(\|\Gamma(A \mid B \cdot C) - (\Gamma_t(A_t \mid B_t \cdot C_t))\|);$$

$$K_h(x) = \exp\left(-\frac{1}{2}\left\|\frac{x}{h}\right\|^2\right);$$

p, s, and h being selected by cross-validation; and g) calculating the influence measure $$I_{B \to A/C} = \ln\left(\frac{|\sum \gamma(\Gamma_t, (A_t \mid \{\} \cdot C_t))|}{|\sum \gamma(\Gamma_t, (A_t \mid B_t \cdot C_t))|}\right).$$

7. A Method of obtaining a Tomography of the Primary Electric Current (PEC) from the signals originated either from the brain or the heart using an array of external electrical and biomagnetic sensors and a set of anatomical and medical images, the method comprising the steps of:

a) measuring at least one of the electrical and magnetic signals from a sensor array, defining observations for a common time t, designating an EEG/EKG as $o_1(t)$ and a MEG/MKG as $o_2(t)$ respectively, obtaining as a result a vector time series defined at time instants $t_I$, $I=1, \ldots, N_t^I$ which specify a lattice of time instants for electrophysiological signals $\Im_1$;

b) specifying lattices of sensor positions as the set of Cartesian coordinates that define the position and orientation of each sensor in a predefined common body reference system, said lattices of sensor positions being designated $\aleph_1$ and $\aleph_2$ for the EEG/EKG and MEG/MKG respectively;

c) selecting an anatomical image and specifying the Cartesian coordinates, in the common body reference system, of its constituent voxels as the lattice of the volume conductor $\Re_\nu$ having points $r_\nu$;

d) specifying for each point $r_\nu$ of $\Re_\nu$, the probability $p(s, r_\nu)$ of that voxel belonging to a given tissue type s thus defining an Anatomical Atlas;

e) Labeling each point $r_\nu$ of the lattice of a volume conductor with a tissue type that has the highest probability, that is $s_\nu = \arg \max_\nu(p(s, r_\nu))$;

f) specifying for each point $r_\nu$ of the lattice of the volume conductor $\Re_\nu$, a conductivity value corresponding to the tissue label $s_\nu$, said values being taken from a predefined set of conductivities, designated as the conductivity profile $\sigma$;

g) selecting a label b that indicates excitable tissue in order to define:
a probability $p(b, r_\nu)$ of excitable tissue for each points $r_\nu$,
a set $\Re_g$ of $N_g$ points $r_g$ for which said probability is non-zero, and
a probability function $p_g = p(b, r_g)$ defined on $\Re_g$;

h) calculating an electric $K_1$ and magnetic $K_2$ lead field matrices by a vector boundary element method such that, given $\sigma$, $\aleph_1$, $\aleph_2$, $\aleph_g$, and $\aleph_\nu$, the following equations hold: $o_1(t) = K_1 f_1(t)$ and $o_2(t) = K_2 f_2(t)$, where $f_1(t)$ and $f_2(t)$ are used interchangeably to denote the PEC;

i) selecting one or more of images selected from the group consisting of the following functional modalities: functional Magnetic Resonance (fMRI), Positron Emission Tomography (PET), and Single Photon Emission Computed Tomography (SPECT), and defining $o_3(t)$, $o_4(t)$, and $o_5(t)$ observations, respectively;

j) specifying the lattices of voxel positions as the set of Cartesian coordinates, in the common body reference system, for each selected functional image, said lattices being designated $\aleph_3$, $\aleph_4$, and $\aleph_5$ for fMRI, PET, and SPECT respectively;

k) specifying the lattices of time instants $t_I$, $I=1, \ldots, N_t^m$ for which each selected functional image m has been sampled, in a common time scale with $\Im_1$, said lattices being designated $\Im_3$, $\Im_4$, and $\Im_5$ for fMRI, PET, and SPECT respectively;

l) calculating an aggregation operator $K_m$ that expresses our knowledge that the ideal functional indicator $f_m(t)$ associated to a m-th image modality (m=3,4,5) defined on $\Re_\nu$ and $\Im_m$ is modified by the image formation process according to a transformation $o_m(t)=(K_m * f_m)(t)$ which:

reduces a spatial resolution of $f_m(t)$ from that of $\Re_\nu$ to that of $\aleph_m$, and reduces the temporal resolution of $f_m(t)$ from that of $\Im_1$, to that of $\Im_m$;

m) calculating the physiological operator $H_m$ that expresses our knowledge that the neural or cardiac tissue activation a(t) defined on $\Re_g$ and $\Im_m$ produces physiological processes associated to the m-th image modality according to the transformation $f_m(t)=(H_m \cdot a)(t)$;

n) calculating estimates of the PEC by joint estimation of all the $f_m(t)$ and of a(t) for all observed m, said estimation comprising steps of:
  i. assigning arbitrary initial values to the $f_m(t)$ and a(t),
  ii. iteratively modifying the values of $f_m(t)$ and a(t),
  iii. calculating a probability measure p which increases when values of $f_m(t)$ and a(t) simultaneously
    Reconstruct the $o_m(t)$ with small error as quantified by a risk function, and
    Have a small norm in a given Besov space, and
  iv. Continuing step (ii) until the probability measure p does not increase;

o) defining $\gamma_m(t)=f_m(t)$, m=1, 2, 3, 4, 5, and $\gamma_6(t)=a(t)$;

p) calculating from $\gamma_m(t)$ the following quantities:
  a vector $s^m=\{s_j^m\}$ that quantifies the magnitude of $\gamma_m(t)$ for $r_t \epsilon \Re_g$, and
  a value $I_{B \to A/C}$ that quantifies the directed influence of brain or heart region B on region A that is not due to the activity coming from region C;

q) calculating probabilities $p_G(s_i^m)$ and $p_G(s_{i \to j}^m)$ that the magnitudes and influences obtained for vector $s^m=\{s_j^m\}$ and $I_{B \to A/C}$ are typical of a given reference group G; and r) coding the values of $p_G(s_i^m)$ and $p_G(s_{i \to j}^m)$ by means of a color scale and displaying said codes overlaid on the selected anatomical image highlighting statistically significant regions by thresholding to zero those values beneath a chosen significance level to obtain a statistical parametric map for the Tomography of PEC.

8. The method defined in claim 7, wherein the common reference system is a Talairach coordinate system.

9. The method defined in claim 7, wherein the anatomical atlas is selected from the group consisting of following variants:

a) as an Individual Anatomical Atlas by the extraction of tissue probabilities of anatomical images obtained for the specific subject under study being at least one of the following types: Computed Axial Tomography (CAT), Magnetic Resonance Images (MRI), and post-mortem sections of the head; and b) as a Probabilistic Anatomical Atlas by one of a rigid or elastic transformation of the subject's volume conductor lattice in order to ensure the best correspondence possible to a canonical volume conductor lattice for which a tissue probability distribution has obtained from a sample of normal or pathological anatomical images.

10. The method defined in claim 7, wherein the computation of the Electric and Magnetic Lead Fields matrices by a vector boundary element method that comprises the steps of:

a) specifying the positions of the sensors for the lattice of EEG/EKG and MEG/MKG modality $\aleph_1$ and $\aleph_2$;

b) specifying the positions $r_g$ and $r_\nu$ in the lattice of the generating volume $\Re_g$, and of the volume conductor $\Re_\nu$ respectively;

c) specifying the conductivity profile using an approximation such that each set of tissue labels constitutes a collection of N embedded regions for which a conductivity value is constant, $\sigma=\{\sigma_1, \ldots, \sigma_N\}$;

d) calculating numerically values for ohmic current densities $j_{kV}=j_k(r_\nu)$ and $j_{kV}^\omega=j_k(r_\nu,\omega)$ on each $r_\nu$ of the lattice of volume conductor $\Re_\nu$ that belongs to the surfaces limiting the regions by means of the following Linear Algebraic Systems of Equations:

Dc=$c_\infty$−Γc; wherein c=($c_1$; . . . ; $C_N$); said $c_k=\{j_{\nu K}, V=1, \ldots, N_{k,k+1}\}$ for the EEG/EKG or $c_k=\{j_{kV}^\omega, V=1, \ldots, N_{k,k+1}\}$ for the MEG/MKG; $N_{k,k+1}$ is a number point $r_\nu$ that belong to a surface separating the regions k and k+1, wherein matrices Γ and D are being defined as:

$$\Gamma = \frac{1}{4\pi} \begin{pmatrix} \frac{(\sigma_1-\sigma_2)}{\sigma_1}\Gamma_{11} & \frac{(\sigma_2-\sigma_3)}{\sigma_2}\Gamma_{12} & \cdots & \Gamma_{1N} \\ \frac{(\sigma_1-\sigma_2)}{\sigma_1}\Gamma_{21} & \frac{(\sigma_2-\sigma_3)}{\sigma_2}\Gamma_{22} & \cdots & \Gamma_{2N} \\ \vdots & \vdots & \ddots & \vdots \\ \frac{(\sigma_1-\sigma_2)}{\sigma_1}\Gamma_{NI} & \frac{(\sigma_2-\sigma_3)}{\sigma_2}\Gamma_{N2} & \cdots & \Gamma_{NN} \end{pmatrix}$$

$$D = \begin{pmatrix} \alpha_1 I_{N_{1,2}} & 0 & \cdots & 0 \\ 0 & 0 & & \vdots \\ \vdots & & \ddots & 0 \\ 0 & \cdots & 0 & \alpha_N I_{N_{N,N}} \end{pmatrix}$$

where $\alpha_j = \frac{(2\sigma_j + \sigma_{j+1})}{3\sigma_j}$;

$$\Gamma_{jk} = \begin{pmatrix} \Gamma_1^k(r_1^j) & \cdots & \Gamma_{N_{k,k+1}}^k(r_1^j) \\ \vdots & \ddots & \vdots \\ \Gamma_1^k(r_{N_{j,j+1}}^j) & \cdots & \Gamma_{N_{k,k+1}}^k(r_{N_{j,j+1}}^j) \end{pmatrix};$$

$r_i^j$ labels an i-th point of $\Re_\nu$ that belong to j-th surface; $c_\infty=(c_\infty^1; \ldots; c_\infty^N)$ with $c_\infty^k=\{j_{kV}^\infty, V=1, \ldots, N_{k,k+1}\}$ for the EEG/EKG and $c_\infty^k=\{j_{kV}^{\omega\infty}, V=1, \ldots, N_{k,k+1}\}$ for the MEG/MKG, wherein the magnitudes $j_{kV}^\infty=j_{k\infty}(r_\nu)$ and $j_{kV}^{\omega\infty}=j_{k\infty}(r_\nu,\omega)$ are evaluated from the expressions:

$$j_{k\infty}(r) = -\frac{I_{\theta r}}{4\pi} \nabla \cdot (g(r,r_\theta) - g(r,r_r))$$

-continued $$j_{k\infty}(r, \omega) = \frac{i\omega}{4\pi} \sum_{k=1}^{N} (\sigma_k - \sigma_{k+1}) \oint_{S_{k,k+1}} g(r, r') \times b_c(r', \omega) dr'^2$$

wherein $b_c(r',\omega)$ is a magnetic field generated by a low frequency AC current passing through a single coil in an infinite and homogeneous volume conductor, and the function $$\Gamma_n^k(r) = \int_{\Delta_n^k} \nabla' g(r, r') \cdot dr'^2 - \int_{\Delta_n^k} \nabla' g(r, r') \circ dr'^2$$

where $g(r_g, r')$ is a Green Function of the infinite domain e) calculating the electric and magnetic lead field in each compartment of $j.(r)$ an IPHC by using reciprocity theorems:

$$k_{eg} = -\frac{j_j(r_g)}{\sigma_j I_{cr}}$$

at the lead electrode "er", and $$k_{eg} = -\frac{j_j(r_g, \omega)}{i\omega\sigma_j I_c(\omega)\Delta S_c}$$

at the coil "co", respectively, the ohmic current densities being evaluated at any point $r_g$ of the lattice of the generating volume $\mathfrak{R}_g$ by the use of the following expressions:

Electric Lead Field:

$$j_j(r_g) = j_{k\infty}(r_g) - \frac{1}{4\pi} \sum_{k=1}^{N} \frac{(\sigma_k - \sigma_{k+1})}{\sigma_k} \sum_{V=1}^{N_{k,k+1}} \Gamma_V^k(r_g) j_{kV}$$

Magnetic Lead Field:

$$j_j(r_g, \omega) = j_{k\infty}(r_g, \omega) - \frac{1}{4\pi} \sum_{k=1}^{N} \frac{(\sigma_k - \sigma_{k+1})}{\sigma_k} \sum_{V=1}^{N_{k,k+1}} \Gamma_V^k(r_g) j_{kV}^\omega; \text{ and}$$

f) calculating the Electric $K_1 = \{k_{eg}{}^r\}$ and Magnetic $K_2 = \{k_{eg}{}^r\}$ Lead Fields matrices specifying a row of said matrices for each sensor (EEG/EKG $e = 1, \ldots, N_e$ and MEG/MKG $c = 1, \ldots, N_c$) and a column for each point of the lattice of the generating volume $r_g \in \mathfrak{R}_g$.

11. The method defined in claim 7, wherein the calculation of the aggregation operator $K_m$ associated to the m-th image modality (i=3, 4, 5) is defined by the following operation $$(K_m * f_m)(t) = \sum_{t_l \in \mathcal{J}} \sum_{r_g \in \mathcal{R}_g} w_m(g, l) K_m(r_g, t, t_l) f_m(r_g, t_l)$$

of which simple local averaging is obtained by specifying $$w_m(g, l) = \frac{1}{N_g + N_l^m}.$$

12. The method defined in claim 7, wherein the estimation of the PEC $f_1(t)$ for a given subject comprises steps of:
a) assigning initial values to the following sets of variables:
1) tissue activation $a(t) = [a(r_g, t)]_{r_g \in \mathfrak{R}_g}$ for each point $r_g$ of $\mathfrak{R}_g$
2) functional indicators $f_m(t) = [f_m(r_g, t)]_{r_g \in \mathfrak{R}_g}$ for each point $r_g$ of $\mathfrak{R}_g$ where $f(t) = [f_m(t)]_{1 \leq m \leq M}$ denotes the totality of measurement modalities obtained for the subject,
3) hyperparameter of the activation $\Theta_a$,
4) hyperparameter of the intrinsic noise of the functional indicators $\Theta_\beta = [\Theta_{\beta_m}]_{1 \leq m \leq M}$, and
5) Hyperparameter of an instrumental noise $\Theta_e = [\Theta_{e_m}]_{1 \leq m \leq M}$;
b) computing a posteriori probability:

$$P(a(t), \Theta_a, f(t), \Theta_\beta, \Theta_e \mid o(t)) \propto$$

$$\prod_{m=1}^{M} I_{o_m}(o_m(t) - (K_m * f_m)(t) \mid \Theta_{e_m}) \times \prod_{m=1}^{M} \pi_{f_m}(f_m(t) - (H_m \cdot a)(t) \mid \Theta_{\beta_m}) \times$$

$$\prod_{m=1}^{M} \{\pi_{\Theta_{a_m}}(\Theta_{e_m}) \cdot \pi_{\Theta_{\beta_m}}(\Theta_{\beta_m})\} \times \pi_a(a(t) \mid \Theta_a) \times \pi_{\Theta_a}(\Theta_a)$$

that comprises the following multiplicative terms:
1) likelihood terms $I_{o_m}$ for each modality m $I_{o_m}(o_m(t) - (K_m * f_m)(t) \mid \Theta_{e_m}$,
2) the a priori probabilities for the functional indicators $\pi_{f_m}(f_m(t) - (H_m \cdot a)(t) \mid \Theta_{\beta_m}$,
3) the a priori probability for the activation $\pi_a(a(t) \mid \Theta_a)$,
4) the a priori probability for the hyperparameters of the activation $\pi_{\Theta_a}(\Theta_a)$,
5) the a priori probabilities for the hyperparameters of the intrinsic noise of the functional indicators, $\pi_{\Theta_{\beta_m}}(\Theta_{\beta_m})$, and
6) the a priori probabilities for the hyperparameters of the instrumental noise; $\pi_{\Theta_{e_m}}(\Theta_{e_m})$;
c) iteratively modifying the parameters $a(t)$, $\Theta_a$, $f(t)$, $\Theta_\beta$, $\Theta_e$ until a maximum value of the a posteriori probability is achieved, said modification being carried out according to a scheme selected from the group consisting of:
1. successive maximization of $P(a(t), \Theta_a, f(t), \Theta_\beta, \Theta_e \mid o(t))$ for subsets of the parameters, while maintaining fixed all the others, "Iterated Conditional Maximization" (ICM),
2. successive maximization of $P(a(t), \Theta_a, f(t), \Theta_\beta, \Theta_e \mid o(t))$ for subsets of the parameters, fixing the other param eters to their expected value, "Expectation Maximization" (EM), and 3. choosing the mode of the distribution of $P(a(t),\Theta_a, f(t),\Theta_\beta,\Theta_e|o(t))$ obtained by means of Monte Carlo Markov Chain methods (MCMC).

13. The method in claim 12, wherein electrophysiological observations $o_m(t)$ m=1,2 for the estimation of $f_1(t)$ is selected from the group consisting of: EEG alone, MEG alone, and EEG and MEG together.

14. The method in claim 12, wherein the electrophysiological observations $o_m(t)$ m=3, 4, 5 for the estimation of $f_1(t)$ are selected from the group consisting of: fMRI alone, PET alone, SPECT alone, fMRI and SPECT, fMRI and SPECT, and PET and SPECT.

15. The method in claim 12, wherein the calculation of the likelihoods $I_{o_m}(o_m(t)-(K_m*f_m)(t)|\Theta_{e_m}$ comprise the following steps:
   a) selecting the use of either e insensitive polynomial risk or a generalized polynomial risk $R_x[x|\Theta_x]$ for the specific purpose of evaluating non gaussian likelihoods;
   b) calculating a discrepancy vector $\Delta = o_m(t)-(K_m*f_m)(t)$;
   c) resetting a(t) as a function of the hyperparameters $\Theta_{e_m}$;
   d) calculating $R_x^C[\Delta|\Theta_x]$, the risk of $\Delta$; and
   e) calculating $I_{o_m}(\Delta|\Theta_{e_m}) = \exp(-BR_x^C[\Delta|\Theta_x])$ where is a preselected constant.

16. The method in claim 12, wherein the calculation of the a priori probability $\pi_{f_m}(f_m(t)-(H_m \cdot a)(t)|\Theta_{\beta_m}$ for the functional indicators comprises the following steps:
   a) selecting indices m, n, s of the Besov space $B_{n,s}^m$, with the purpose of defining the smoothness of the estimated functional indicator, a particular but not exclusive choice being m=1, n=1, s=1 which defines the "algebra of bumps;"
   b) calculating the discrepancy vector $\Delta = f_m(t)-(H_m \cdot a)(t)$;
   c) resealing the $\Delta$ as a function of the hyperparameters $\Theta_{\beta_m}$;
   d) calculating $\|\Delta\|_{B_{n,s}^m}$, the norm of the $\Delta$ in $B_{n,s}^m$, said calculation being carried out by first expanding $\Delta$ as $$\Delta = \sum_k F_k \cdot \Psi_k$$

where the $\Psi_k$ belong to a Dictionary of Atoms and then calculating $$\|\Delta\|_{B_{n,s}^m} \approx \sum_k a_k \cdot \|F_k\|^m;$$

and
   e) calculating $\pi_{f_m}(\Delta|\Theta_{B_m}) = \exp(-C\|\Delta\|_{B_{n,s}^m})$ where C is a preselected constant.

17. The method in claim 12 wherein the calculation of the a priori probability of the activation $\pi_a(a(t)|\Theta_a)$ comprises the following steps:
   a) calculating a non decreasing function h(·) of a probabilistic atlas h($p_g$);
   b) calculating the norm $\|a(t)\|_{B_{n,s}^m}$; and
   c) calculating $\pi_a(a(t)|\Theta_a) = \exp(-Dh(p(s,r_g))-E\|a(t)\|_{B_{n,s}^m})$, where D and E are prespecified constants.

18. The method in claim 16, wherein the a priori probability for the following specific form:

$$\pi_{f_1}(f_1(t)-(H_1 \cdot a)(t)|\Theta_{\beta_1}) = \pi_1(f_1(t)-Ma(t)|\Theta_1)\pi_2(\mu|\Theta_2)$$

where $\pi_1$ and $\pi_2$ are a priori probabilities specified as in claim 15, $$M = \begin{bmatrix} \mu_1 & 0 & \cdots & 0 & 0 \\ 0 & \mu_2 & \cdots & 0 & 0 \\ \cdots & \cdots & \mu_1 & \cdots & \cdots \\ 0 & 0 & \cdots & \mu_{N_g-1} & 0 \\ 0 & 0 & \cdots & 0 & \mu_{N_g} \end{bmatrix}$$

$$\mu = \begin{bmatrix} \mu_1 \\ \mu_2 \\ \cdots \\ \mu_{N_g} \end{bmatrix}$$

where the $\mu_g$ are the orientations of the PEC for each point of $\Re_g$.

19. The method in claim 18, wherein the a priori probability $\pi_2(\mu|\Theta_2)$ defined in claim 17 is calculated by an expression selected from the group of expressions consisting
   $\pi_2(\mu|\Theta_2) = \exp(-\|\Lambda_s \cdot \mu \cdot \Lambda_m\|_{B_{n,s}^m})$ where $\Lambda_s$ is a diagonal matrix that specifies the degree of smoothness that will be imposed at each point of $\Re_g$ and $\Lambda_m = W \cdot P$, where W is a prespecified weighting matrix and P is a diagonal matrix containing $p_g$ for all $r_g$, and
   by means of successive evaluation of marginal distributions of $\pi_2(\mu_g|\Theta_2) = p_g \cdot N(0,\sigma_A^2) + (1-p_g) \cdot N(0,\sigma_B^2)$ with $N(0,\sigma^2)$ a univariate gaussian distribution with mean zero and standard deviation $\sigma$, $\sigma_A^2$, and $\sigma_B^2$ being constants selected to be large and small respectively with respect to the expected variation of the orientations.

20. The method in claim 12, wherein the calculations are carried out for at least one of $o_1(t)$ and $o_2(t)$ in the frequency domain by specifying:
   that the electrical signals have been subjected to the Fourier transform, t now denoting frequency;
   $I_{o_m}(o_m(t)-(K_m*f_m)(t)|\Theta_{e_m}) = N_R^{2P}(0,\Sigma_e)$, where $N_R^{2P}(\mu_x, \Sigma_x)$ denotes the multivariate real gaussian distribution with mean and variance $(\mu_x, \Sigma_x)$
   $\pi_{f_m}(f_m(t)-(H_m \cdot a)(t)|\Theta_{\beta_m}) = N_R^{2P}(0,0)$, $H_m = I$, an identity matrix $$\pi_a(a(t)|\Theta_a) = N_R^{2P}(0,\Sigma_a)$$

$$\pi_{\Theta_a}(\Theta_a) = \|\sum_a\|^{-\frac{\alpha}{2}} \exp\left(-\frac{1}{2} Tr\left(Q \sum_a^{-1}\right)\right)$$

a natural conjugate a priori distribution for complex Wishart matrices, where $\alpha$ and Q are prespecified in accordance with prior knowledge, and $\pi_{\Theta_{\beta m}}(\Theta_{\beta m})$ and $\pi_{\Theta_{\epsilon m}}(\Theta_{\epsilon m})$ being constants defining improper priors.

* * * * *